United States Patent [19]

Binderup

[11] 4,229,443

[45] Oct. 21, 1980

[54] DERIVATIVES OF PENICILLANIC ACID

[75] Inventor: Ernst T. Binderup, Tåstrup, Denmark

[73] Assignee: Leo Pharmaceutical Products, Ltd. A/S, Ballerup, Denmark

[21] Appl. No.: 806,358

[22] Filed: Jun. 14, 1977

[30] Foreign Application Priority Data

| Jun. 29, 1976 [GB] | United Kingdom | 27107/76 |
| Jul. 27, 1976 [GB] | United Kingdom | 31331/76 |
| Feb. 9, 1977 [GB] | United Kingdom | 5436/77 |
| Feb. 15, 1977 [GB] | United Kingdom | 6348/77 |

[51] Int. Cl.$^2$ .............. A61K 31/675; A61K 31/425; A61K 31/43; C07D 499/02

[52] U.S. Cl. .............. 424/200; 260/239.1; 260/245.2 R; 424/246; 424/256; 424/266; 424/267; 424/270; 424/271; 542/401; 542/412; 542/414; 542/417; 542/422

[58] Field of Search ........... 260/239.1, 306.7 C, 260/245.2; 542/414, 401, 417, 412, 422, 266; 424/270, 267, 271, 256, 246, 200

[56] References Cited

U.S. PATENT DOCUMENTS

| 3,755,588 | 8/1973 | Lund | 424/271 |
| 3,957,764 | 5/1976 | Lund | 260/240 G |

FOREIGN PATENT DOCUMENTS

| 1315566 | 5/1973 | United Kingdom | 260/240 G |
| 1427139 | 3/1976 | United Kingdom | 260/240 G |

*Primary Examiner*—Natalie Trousof
*Assistant Examiner*—Vera C. Clarke
*Attorney, Agent, or Firm*—Dann, Dorfman, Herrell & Skillman

[57] ABSTRACT

The present invention relates to new substituted 6β-amidinopenicillanic acids; pharmaceuticallyacceptable salts, easily hydrolyzable esters thereof and salts of such esters; to methods of producing the compounds; to intermediates in their preparation, to pharmaceutical compositions containing the compounds; to dosage units thereof; and to their use.

55 Claims, No Drawings

DERIVATIVES OF PENICILLANIC ACID

DESCRIPTION

The compounds of the present invention have shown increased activity against a series of bacteria which cause infections difficult to combat with the presently available antibiotics.

The present invention relates to new substituted 6β-amidinopenicillanic acids; pharmaceutically acceptable salts, easily hydrolyzable esters thereof and salts of such esters; to methods of producing the compounds; to intermediates in their preparation, to pharmaceutical compositions containing the compounds; to dosage units thereof; and to their use.

The compounds of the invention are carboxylic acids represented by the general formulae I, II, and III:

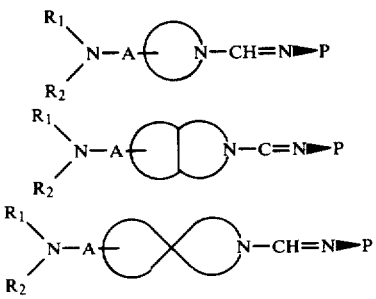

in which -A- stands for a straight or branched, saturated or unsaturated aliphatic hydrocarbon radical, containing from 1 to 6 carbon atoms, which radical optionally can be substituted with an amino radical; $R_1$ stands for hydrogen, or a lower alkyl radical with from 1 to 4 carbon atoms; $R_2$ stands for hydrogen, a lower alkyl radical with from 1 to 4 carbon atoms, or an acyl radical derived from a mono- or dibasic carboxylic acid, sulphuric acid, a sulphonic acid, a sulphinic acid, phosphoric acid, or a phosphonic acid, and $R_2$ can represent an unsubstituted or substituted carbamoyl, guanyl and guanylcarbamoyl radical; $R_1$ and $R_2$ together with the nitrogen atom can form a monocyclic, saturated ring having from 4 to 8 carbon atoms; furthermore $R_1$ and $R_2$ together can represent a radical of the formula

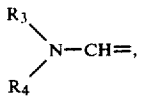

in which $R_3$ and $R_4$ each stands for hydrogen, lower alkyl, phenyl, or phenyl-lower alkyl radicals, or in which $R_3$ and $R_4$ together with the nitrogen atom form a monocyclic, saturated ring having from 4 to 7 carbon atoms; the groupings:

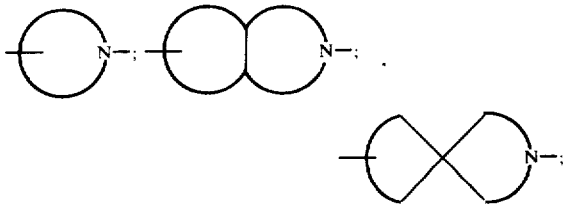

represent saturated, monocyclic, bicyclic or spirocyclic ring systems, respectively, containing from 4 to 11 carbon atoms in total; P stands for the penicillanic acid radical of the formula IV

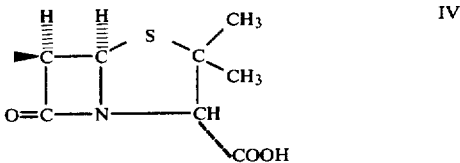

and salts of the compounds of the formulae I, II, and III with pharmaceutically acceptable, non-toxic organic and inorganic acids or bases, and easily hydrolyzable pharmaceutically acceptable, non-toxic esters of the penicillanic acid derivatives of formulae I, II, and III, including diesters of the formula V:

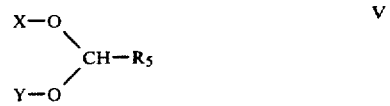

in which X and Y can be the same or different and stand for an acyl radical of one of the compounds of formulae I, II, and III, and Y furthermore can be the acyl radical of other known β-lactam antibiotics, $R_5$ stands for hydrogen, methyl, ethyl, or phenyl, and salts of such esters with pharmaceutically acceptable, non-toxic acids or bases.

More particularly, -A- represents straight or branched aliphatic radicals such as methylene, ethylene, ethylidene, propylene, trimethylene, tetramethylene, propylidene, methyltrimethylene, pentamethylene, methyltetramethylene, dimethyltrimethylene, hexamethylene, ethyltetramethylene, methylpentamethylene, or unsaturated aliphatic radicals such a propenylene, butenylene, pentenylene; hexenylene; hexadienylene; methylpropenylene, dimethylpropenylene, propynylene, butynylene, hexynylene; methylpropynylene, methylpentynylene, 2-penten-4-ynylene and 1-methyl-2-penten-4-ynylene, the above examples, however, not to be construed as limiting the invention, -A- may optionally be substituted with an amino radical which can be an unsubstituted or a mono- or di-lower alkyl substituted amino group or a lower alkanoyl substituted amino group.

It shall be understood, however, that the nitrogen atom(s) shall never be attached to an unsaturated carbon atom.

More particularly, $R_1$ can be hydrogen or a lower alkyl radical having from 1 to 4 carbon atoms as, for instance, methyl, ethyl, propyl, isopropyl, n-butyl, sec-butyl, isobutyl or tert-butyl.

Similarly, $R_2$ stands for hydrogen or a lower alkyl radical as defined for $R_1$, or $R_2$ stands for an acyl radical as, for instance, formyl, acetyl, propionyl, butyryl, isobutyryl, valeryl, isovaleryl, trimethylacetyl, caproyl, crotonyl, glycolyl, benzoyl, phenylacetyl, phenoxyacetyl, glycyl, phenylglycyl or acyl radicals of other amino acids, heterocyclically substituted acyl, e.g. nicotinoyl or

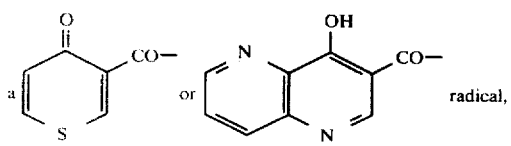

radical, or a monoacyl radical derived from a dibasic acid such as oxalic, malonic, succinic, maleic, fumaric, tartaric, malic or phthalic acids; and when $R_2$ stands for a substituted carbamoyl, guanyl, or guanylcarbamoyl radical, the substituents can be e.g. lower alkyl or phenyl radicals. Further $R_2$ stands for an acyl radical derived from sulphuric acid, a sulphonic, sulphinic, phosphoric or a phosphonic acid such as toluenesulphonic acid, methane- or ethanesulphonic acid, toluenesulphonic acid, lower alkylphosphonic acids etc.

In the formula above $R_3$ and $R_4$ can more specifically be lower alkyl with from 1 to 4 carbon atoms or phenyl-lower alkyl in which the alkyl radical has from 1 to 4 carbon atoms, or $R_3$ and $R_4$ together with the nitrogen atom form a pyrrolidyl, piperidyl, hexahydro-1H-azepin-1-yl or hexahydro-1(2H)-azocin-1-yl radical. More particularly the groupings:

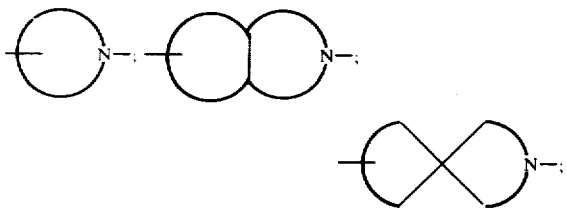

representing saturated monocyclic, bicyclic or spirocyclic ring systems can be pyrrolidyl, piperidyl, hexahydro-1H-azepinyl, octahydro-azocinyl, decahydro-azecinyl, azacyclododecanyl, 3-azabicyclo[3.1.0]hexanyl, 5-azaspiro[2.4]heptanyl, 3-azabicyclo[4.1.0]heptanyl, 3-azabicyclo[3.2.0]heptanyl, 6-azabicyclo[3.1.1]heptanyl, 7-azabicyclo[4.2.0]octanyl,2-azabicyclo[2.2.2]octanyl, 1-azaspiro[5.5]undecanyl, 2-, and 3-azabicyclo[3.3.1]nonanyl 2-azaspiro[4.6]undecanyl, 2-azabicyclo[3.2.1]octanyl, 3-azabicyclo[3.2.1]octanyl, 6-azabicyclo[3.2.1] octanyl, 1-azaspiro[4.5]decanyl, 2-azaspiro[4.5]decanyl, 2-azabicyclo[3.2.2]nonanyl, 3-azabicyclo[4.1.1]octanyl, 2-azabicyclo[2.2.1]heptanyl, 2-azabicyclo[4.3.1]decanyl, 8-azaspiro[4.5]decanyl, 2-azaspiro[5.5]undecanyl, 3-azaspiro[5.5]undecanyl, 3-azabicyclo[3.1.1]heptanyl, 2azabicyclo[4.2.0]octanyl, 2-azaspiro[4.4]nonanyl, 8-azabicyclo[4.3.1]decanyl, 4-azabicyclo[5.3.0]decanyl, 3-azabicyclo[3.3.0]octanyl, 8-azabicyclo[4.3.0]nonyl, the examples above, however, not being construed as limiting the invention.

The salts of the compounds of the invention are in addition to their inner salts (zwitterions) mono-or dibasic salts, formed with non-toxic, pharmaceutically acceptable acids such as hydrochloric acid, phosphoric acid, nitric acid, p-toluenesulphonic acid, acetic acid, propionic acid, citric acid, tartaric acid, maleic acid etc., but any pharmaceutically acceptable, non-toxic inorganic or organic acids can be used as well.

Also included in the invention are salts with pharmaceutically acceptable, non-toxic, inorganic or organic bases, e.g. alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)-amine or tris-(2-hydroxyethyl)-amine, cycloalkylamines, for example dicyclohexylamine, or benzylamines, for example N,N'-dibenzyl-ethylenediamine, and dibenzylamine, without these examples being limiting the invention. Thus for instance other antibiotics with acid or basic character can be used as components of such salts of the compounds of formulae I, II, and III.

The easily hydrolyzable, pharmaceutically acceptable esters of the new compounds are the well known types of esters, e.g. acyloxyalkyl esters, such as alkanoyloxyalkyl esters, e.g. acetoxymethyl and pivaloyloxymethyl esters and the corresponding 1-acetoxyethyl and 1-pivaloyloxyethyl esters, alkoxycarbonyloxyalkyl esters, e.g. methoxycarbonyloxymethyl and 1-ethoxycarbonyloxyethyl esters, lactonyl esters, e.g. phthalidyl esters, or lower alkoxymethyl and acylaminomethyl esters. Other interesting acyloxyalkyl esters are within the scope of the invention, e.g. such esters in which the acyl group is a radical derived from a $\beta$-lactam antibiotic, such as a penicillin, cephalosporin, an amidinopenicillanic acid or clavulanic acid, which esters when hydrolyzed in the host may give rise to enhanced effect. Also other esters can be useful, e.g. the benzyl ester and the cyanomethyl ester.

Appropriately the esters above can be prepared and used in the form of their salts with pharmaceutically acceptable, non-toxic inorganic or organic acids or bases.

The invention comprises all possible diastereomers of the compounds of formulae I, II and III and their esters, and the mixture thereof, in the case when the side chain and/or an ester group contain one or more asymmetric carbon atoms, or double bonds giving rise to cis-trans isomerism. The penicillanic acid moiety has the steric configuration indicated in the formula IV.

A series of substituted 6$\beta$-amidinopenicillanic acids, their salts and easily hydrolyzable esters are disclosed in the British Pat. No. 1,293,590 and other easily hydrolyzable esters of the compounds of British Pat. No. 1,293,590 have been disclosed in the British Pat. Nos. 1,335,718 and 1,405,886.

Surprisingly, the compounds of the present invention have shown increased activity against a series of bacteria which cause infections difficult to combat with the presently available antibiotics. Of special interest in this connection is that the compounds are active against Pseudomonas species which are not sensitive to the compounds of the above mentiond specifications. Compounds of the invention, in which -A- stands for a saturated or unsaturated carbon chain with from 1 to 3 carbon atoms, and in which $R_1$ and $R_2$ stand for hydrogen have in preliminary experiments proved to be of particular interest in the treatment of infections caused by Pseudomonas.

Preliminary experiments also reveal that compounds having from 5 to 8 carbon atoms in the

grouping and a maximum of 7 carbon atoms in the individual rings of the bicyclic and spirocyclic groupings.

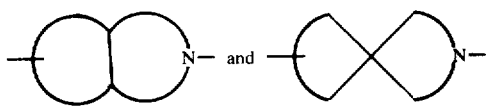

seem to be appropriate, in particular with—but not limited to—a carbon chain -A- containing from 1 to 3 carbon atoms. Generally, such compounds are preferred in which the carbon chain -A- is not attached to a carbon atom adjacent to the nitrogen atom of the monocyclic ring system.

The table below indicates compounds of the invention corresponding to formula I in which $R_1$, $R_2$, -A- and the numbers of the carbon atoms in the ring (n) are as follows:

| $R_1$ | $R_2$ | A | n |
|---|---|---|---|
| H | H | propylene | 4 |
| H | acetyl | trimethylene | 4 |
| ethyl | H | tetramethylene | 4 |
| methyl | propionyl | 1,1-dimethylethylene | 4 |
| H | H | hexamethylene | 4 |
| butyl | butyl | 2-methyltetramethylene | 4 |
| methyl | H | 2-methylpentamethylene | 5 |
| H | guanyl | hexamethylene | 5 |
| H | butyryl | trimethylene | 5 |
| isopropyl | H | tetramethylene | 5 |
| H | H | 2-aminotetramethylene | 5 |
| H | acetyl | 2-acetaminotetramethylene | 5 |
| methyl | methyl | 2-dimethylaminotetramethylene | 5 |
| H | methyl | trimethylene | 6 |
| butyl | H | ethylene | 6 |
| H | H | ethylidene | 6 |
| methyl | tosyl | methylene | 6 |
| H | acetyl | methylene | 6 |
| H | H | 1-propanyl-3-ylidene | 5 |
| H | guanyl | butenylene | 6 |
| methyl | methyl | hexynylene | 5 |
| H | carbamoyl | ethylene | 6 |
| H | guanyl | methylene | 6 |
| methyl | guanyl | propylene | 6 |
| H | H | trimethylene | 7 |
| H | acetyl | 2-methyltrimethylene | 7 |
| methyl | methyl | tetramethylene | 7 |
| methyl | H | ethylene | 7 |
| H | H | methylene | 7 |
| H | carbamoyl | methylene | 7 |
| butyl | H | propylene | 7 |
| H | H | 2-aminopropylene | 7 |
| H | H | methylene | 8 |
| H | acetyl | ethylidene | 8 |
| H | guanyl | ethylene | 8 |
| methyl | H | ethylene | 8 |
| H | guanylcarbamoyl | ethylene | 8 |
| H | H | propylene | 8 |
| H | hemisuccinyl | ethylidene | 8 |
| H | methanesulphonyl | ethylene | 8 |
| H | tosyl | methylene | 9 |
| H | H | ethylene | 9 |
| H | H | methylene | 10 |
| methyl | H | methylene | 10 |
| H | acetyl | ethylene | 10 |
| H | H | methylene | 11 |
| methyl | methyl | methylene | 11 |

The table below indicates compounds of the invention corresponding to formula II in which $R_1$, $R_2$, -A-, and the number of carbon atoms in the rings are as follows, where $n_1$ refers to the heterocyclic part of the ring system, and $n_2$ refers to the total number of carbon atoms in the ring system

| $R_1$ | $R_2$ | A | $n_1$ | $n_2$ |
|---|---|---|---|---|
| methyl | H | ethylene | 3 | 7 |
| H | H | methylene | 6 | 7 |
| H | H | 2-aminopropylene | 6 | 7 |
| H | propionyl | tetramethylene | 4 | 6 |
| ethyl | H | methylene | 4 | 7 |
| methyl | methyl | propylene | 5 | 7 |
| N,N-dimethylaminoethylene | | methylene | 6 | 9 |
| H | H | propenylene | 4 | 7 |
| ethyl | ethyl | hexenylene | 5 | 8 |
| H | carbamoyl | butynylene | 4 | 6 |

The table below indicates compounds of the invention corresponding to formula III in which $R_1$, $R_2$, -A-, and the number of carbon atoms in the rings are as follows, where $n_1$ refers to the heterocyclic part of the ring system, and $n_2$ refers to the total number of carbon atoms in the ring system.

| $R_1$ | $R_2$ | A | $n_1$ | $n_2$ |
|---|---|---|---|---|
| H | H | 1-aminopropylene | 4 | 9 |
| methyl | methyl | 1,1-dimethyl-ethylene | 4 | 9 |
| aminomethylene | | methylene | 4 | 10 |
| methyl | H | ethylene | 5 | 10 |
| ethyl | ethyl | trimethylene | 5 | 10 |
| H | H | propenylene | 5 | 9 |

The above examples, however, shall in no way be construed as limiting the invention.

In the table below the antibacterial activity of the compound of Example 1, the 6-[4'-(3''-aminopropyl)-1'-piperidyl-methyleneamino]penicillanic acid hydrochloride, in the table called EB 686, is compared to that of the known compounds Ampicillin and Mecillinam (a compound of the above mentioned British Pat. No. 1,293,590).

TABLE

| | *IC$_{50}$ (μg/ml) | | |
|---|---|---|---|
| Organism | Ampicillin | Mecillinam | EB 686 |
| Pseudomonas aeruginosa BA 2 Leo strain | >100 | >100 | 16 |
| Pseudomonas aeruginosa PS 18s | 50 | >100 | 5.0 |
| E.coli HA 2 Leo strain | 1.3 | 0.016 | 0.016 |
| E.coli W3110 (R$_{TEM}$) | >100 | 2.0 | 0.5 |
| Klebsiella pneumoniae AT CC 10273 | 79 | ~1 | 0.04 |
| Enterobacter cloacae P 99 | >100 | 0.1 | 0.02 |
| Salmonella typhimurium NCTC 5710 | 0.4 | 0.05 | 0.016 |
| Salmonella cholerasuis NCTC 5735 | 0.25 | 0.05 | 0.0063 |

*IC$_{50}$ means the concentration required for a 50% inhibition of growth.

The invention also comprises methods for the preparation of the compounds of the invention. In one embodiment the compounds are prepared by reacting a reactive derivative of an amide or a thioamide of the general formulae VI, VII, and VIII

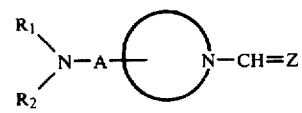

-continued

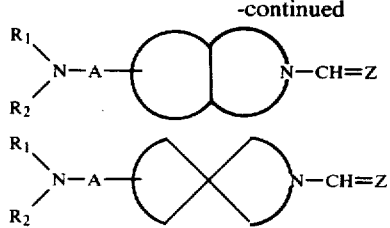

in which R₁, R₂, A, and the groupings:

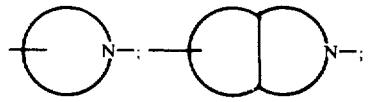

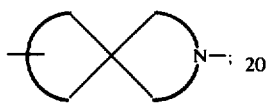

are as defined hereinabove, or

is, if necessary, protected or replaced by a nitro or an azido group, or a halogen atom, whereas Z stands for oxygen or sulphur, with a 6-aminopenicillanic acid derivative of the general formula IX:

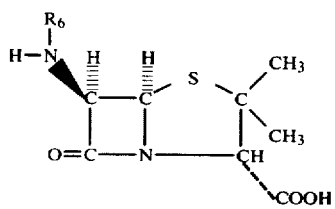   IX in which $R_6$ is hydrogen or a trialkylsilyl group, or a salt thereof, or with an ester of an intermediate of formula IX, e.g. a trialkylsilyl, benzyl or cyanomethyl ester or an easily hydrolyzable ester as defined above or an ester of the formula X:

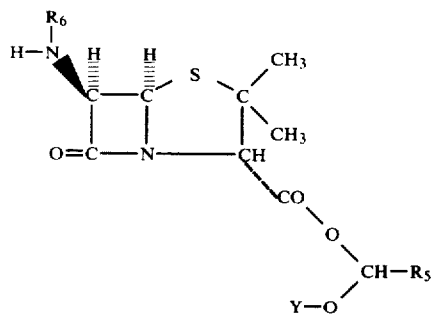   X in which $R_5$, $R_6$, and Y have the meaning hereinbefore defined.

If a silyl ester of the intermediate of formula IX is used, the reaction must be followed by a hydrolysis or alcoholysis to provide the free acids of the invention, which also may be obtained by cleavage of the other esters obtained by the reaction.

The preparation of the above mentioned 6-aminopenicillanic acid derivatives is known from the literature.

In the case where in the compounds of formulae I, II, or III one or both of $R_1$ and $R_2$ stand for hydrogen or

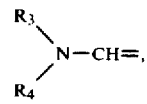

$R_3$ and/or $R_4$ being hydrogen, or if the carbon chain -A- is substituted with a reactive amino radical, it can be necessary to protect the

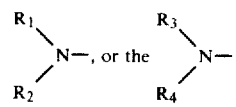

groupings, and, if present, the amino radical temporarily during the process with protecting groups more particularly described below. Alternatively, instead of the starting materials of formulae VI, VII or VIII can be used a compound which instead of the

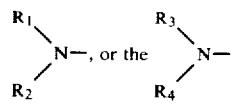

groupings and, if present, the amino radical, has a group, e.g. a nitro or an azido group, or a halogen atom, which after the reaction with the compound of formulae IX or X can be transformed into an amino group under mild conditions. These intermediates are also new compounds constituting as such a part of this invention. Also they have in themselves interesting antibacterial properties, especially the azido compounds.

The starting materials of formulae VI, VII, and VIII can be prepared by conventional methods known to the man skilled in the art. The reactive derivatives of these starting materials are in the following described more in detail.

The amides or thioamides of formulae VI, VII, and VIII can be transformed by well-known methods into reactive derivatives such as acid amide halides or acid amide acetals or iminium-ethers or -thioethers, e.g. acid amide dialkyl sulphate complexes or complexes with the well-known Meerwein reagent (triethyloxonium tetrafluoroborate). The acid amide halides are preferably the chlorides or bromides and they can be prepared by treating the amides with halogenating agents. It is preferred to use halogenating agents which throughout the reaction form gaseous by-products, such as phosgene, oxalyl halides, or thionyl halides, but others may also be used. The reaction can be performed in an inert, dry, organic solvent, e.g. ether or toluene, in which the amide halide will in most cases be insoluble and from which it can be isolated by filtration after the reaction is completed. The acid amide halides are hygroscopic and rather unstable and are therefore preferably used in the next step without purification. However, the amide halide may also be prepared in e.g. alcohol-free chloroform solution and used directly for the next step, advantage being taken of the harmless character of the gaseous by-products (CO, CO$_2$, SO$_2$, COS).

Useful acid amide dialkyl sulphate complexes as intermediates can be prepared by treating the corresponding amides with a dialkyl sulphate, preferably dimethyl sulphate, under well-known conditions. By treating the acid amide dialkyl sulphate complexes or acid amide halides with a sodium C$_1$ to C$_6$ alcoholate, e.g. sodium methoxide, acid amide acetals of the general formulae XI, XII, and XIII

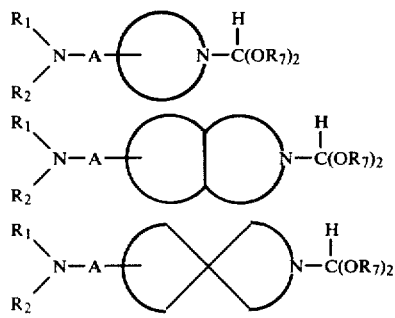

in which R$_1$, R$_2$, A, and the groupings:

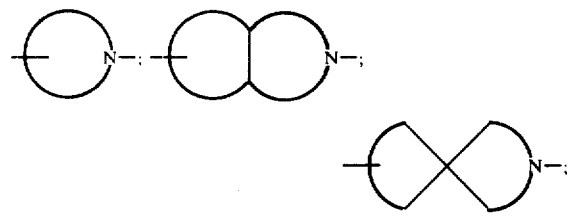

have the meaning hereinbefore defined, or

is, if necessary, protected or replaced by a nitro or an azido group or a halogen atom, whereas R$_7$ stands for an alkyl group containing 1 to 6 carbon atoms, are formed, which acetals may also be used in the preparation of compounds of formulae I, II, and III.

When acid thioamides are used as starting materials, a reactive derivative in form of an acid thioamide alkyl halide complex can be formed by treatment with an alkyl halide, e.g. a C$_1$ to C$_6$ alkyl iodide. This reaction is well known from the chemical literature.

The reaction conditions for the reaction between the amide derivative and the compound of formulae IX or X depend on the reaction components used in the process. For instance, when an acid amide acetal or a dialkyl sulphate complex or another iminium ether or thioether is used in the reaction with the compound of formulae IX or X, the reaction is performed in an organic solvent and at a temperature depending upon the reaction components. When an acid amide halide is used, the reaction is usually performed in an inert organic solvent, which is dry and free from traces of alcohol, preferably chloroform, in which the reaction components are soluble, but solvents in which the starting materials are insoluble, e.g. ether, may also be used. The reaction is performed with cooling and, if necessary, in the presence of at least one equivalent of a tertiary amine, for example trimethylamine, triethylamine, N,N-diisopropylethylamine or N-methylmorpholine.

The reaction time depends on the reactants, the temperature and the solvents used in the process.

In the preparation of compounds of formulae I, II, and III, it is also possible to use as starting material a trialkylammonium salt of 6-APA, which is reacted with e.g. an acid amide acetal under the same conditions as mentioned above. Such reactions are known from the specification to our British Pat. No. 1,417,099.

In another embodiment the compounds of the present invention can be prepared by reacting an amine of one of the formulae XIV, XV, and XVI:

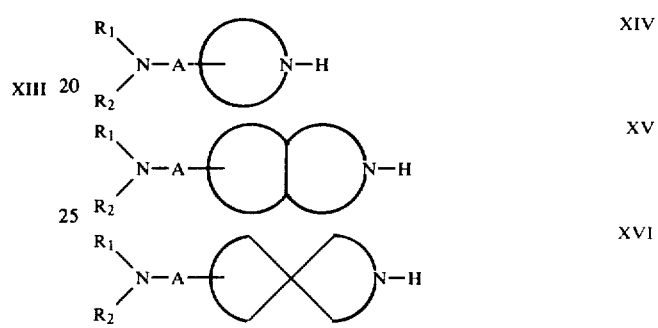

in which R$_1$, R$_2$, A and the groupings:

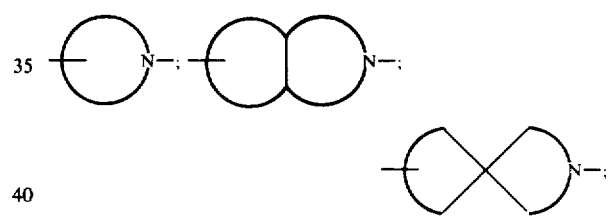

are as hereinbefore defined, or

is, if necessary, protected or replaced by nitro or azido, or a halogen atom with a 6-alkoxymethyleneaminopenicillanic acid ester obtained either by reacting a compound of formulae IX or X with a 1,1-dihalomethyl-alkyl ether, preferably 1,1-dichlorodimethyl ether, in the presence of a tertiary organic base; the reaction can be performed without isolation of the intermediate formed by the process, which in the example mentioned above is supposed to be a 6-N-methoxymethylene derivative of the compound of formula IX or X. The reactions are performed below or at room temperature and in the presence of an inert solvent, e.g. chloroform, or ether. However, a more favourable method to obtain a 6-alkoxymethyleneaminopenicillanic acid ester consists in reacting an ethereal solution of a compound of formulae IX or X with a formimidic ester hydrochloride, preferably isopropyl formimidic ester hydrochloride, preferably at room temperature and for the time necessary to accomplish the reaction. Ammonium chloride is thereby precipitated leaving an ethereal solution of a 6-alkoxymethyleneaminopenicillanic acid ester.

The reaction products of formulae I, II, or III can be purified and isolated in usual manner and may be obtained either in the free state or in the form of salts or esters. The free acids can also be obtained from the esters by chemical or enzymatic hydrolysis or a mild hydrogenolysis, and if the free acids are the reaction products, the salts and esters can be prepared therefrom by methods known from the literature.

Protection of the amino group

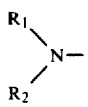

or, if present,

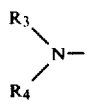

of the formulae I, II, or III, and protection of a reactive amino radical attached to the carbon chain -A- in the formulae I, II, and III, may, if necessary, take place by methods known from the peptide chemistry. Amongst many known and suitable protecting groups can be mentioned e.g. a benzyloxycarbonyl radical, a p-halo-, p-nitro-, or p-methoxybenzyloxycarbonyl radical, a β,β,β-trichloroethyloxycarbonyl or an allyloxycarbonyl radical; or a sulphur containing radical, such as a triphenylmethylsulphenyl radical, an arylsulphenyl radical, e.g. an o-nitro-phenylsulphenyl radical; a triphenylmethyl radical, a tertiary butoxycarbonyl radical, or a radical obtained by reacting the free amino group with a β-dicarbonyl compound such as acetylacetone, benzoylacetone or acetoacetic esters or amides to form enamines, or to form Schiff bases with e.g. formaldehyde, acetaldehyde etc. In general any group which can be split off by reduction, by mild acid hydrolysis or by other mild reactions not damaging the β-lactam ring will be suitable.

Whatever protection of the amino group has been used or, alternatively, whatever conventional replacement of the amino group has been used, the amino group can be established by well-known methods, such as hydrogenation, hydrolysis or aminolysis.

In general, the compounds of formulae I, II, and III in which both R₁ and R₂ are hydrogen can be obtained from the corresponding nitro, azido or halo compounds by hydrogenation or aminolysis, respectively.

In another embodiment of the invention the compounds of the invention in which R₁ and/or R₂ are hydrogen can be exposed to acylation or alkylation by well-known methods to form the compounds of the invention in which R₁ and R₂ have the other desired definitions given hereinbefore.

Also the radical

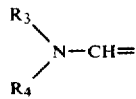

can optionally be introduced in a separate final step by methods analogous to the main reaction described above for obtaining the amidinopenicillanic acid structure.

Similarly, an amino group attached to the carbon chain -A- can be acylated or alkylated as above, or be introduced by converting e.g. an azido or nitro group or a halogen atom into an amino group followed, if desired, with an acylation or alkylation.

When by the above process a salt or an ester is obtained this can be transformed into the free acid in known manner and, vice versa, it will be evident that the free acid or a salt can be esterified by well-known methods.

According to one of these methods a compound of formulae I, II, or III can be transformed into the corresponding α-halo-alkyl ester, which then can be reacted with a salt of the acid in question to form an acyloxyalkyl ester.

It is also an object of the present invention to provide an antibacterial pharmaceutical composition for use in the treatment of infectious diseases, which contains as an active ingredient a 6-aminopenicillanic acid derivative of the formulae I, II, or III given hereinbefore.

For parenteral and topical use the compounds of formulae I, II, and III or their salts are preferred. These can also in some cases be used orally. However, for oral use it is in most cases advantageous to use an easily hydrolyzable ester of the compounds, because such esters are generally better absorbed than the corresponding acids or salts. The esters have no antibacterial activity per se, but they are during or after the absorption hydrolyzed with liberation of the corresponding free acids.

The active ingredient can be used as such or can be mixed up with a carrier and/or an auxiliary agent.

In such compositions, the proportion of therapeutically active material to carrier substance and auxiliary agent can vary between 1% and 95%. The compositions can either be worked up to pharmaceutical forms of presentation such as tablets, pills or dragees, or can be filled in medical containers such as capsules, or as far as suspensions are concerned filled into bottles. Pharmaceutical organic or inorganic solid or liquid carriers suitable for enteral, parenteral or topical administration can be used to make up the composition. Gelatine, lactose, starch, magnesium stearate, talc, vegetable and animal fats and oils, gum, polyalkylene glycol, or other known carriers for medicaments may all be suitable as carriers.

In the pharmaceutical compositions the compounds of the invention can be used together with other suitable therapeutically active components, preferably with other antibacterially active compounds, such as β-lactam-antibiotics, e.g. penicillins or other amidinopenicillanic acid derivatives, and cephalosporins. Also other antibacterially active substances are of interest in this connection, e.g. trimethoprim and aminoglycosides. In many cases, e.g. in combinations with penicillins like ampicillin, amoxycillin, or carbenicillin, or cephalosporins like cephalothin, cephazolin or cephalexin, a synergistic effect is observed which is of importance in many clinical stituations. Also a depression of development of resistance can be obtained by a combination therapy. In such compositions the ratio between the active components appropriately is between 1:20 and 20:1, preferably within the ratio 1:5 and 5:1.

The compounds of the invention can also be used together with a β-lactamase inhibitor, such as clavulanic acid.

Another object of the invention resides in the selection of a dose of the compounds of the invention which can be administered so that the desired activity is achieved without simultaneous secondary effects.

The copounds are conveniently administered in dosage units containing amounts corresponding to from 0.025 g to 2.5 g of the free acid of formulae I, II and III and preferably to from 0.05 g to 1.5 g depending on which microorganisms are involved. By the term "dosage unit" is meant a unitary, e.g. a single dose capable of being administered to a patient, and which may be readily handled and packed, remaining as a physically stable unit dose, comprising either the active material as such or a mixture of it with a pharmaceutical carrier.

Similarly, for infusion, the compounds of the invention are given in doses up to 10 g in aqueous solution.

For parenteral use, e.g. injections, the compounds of the invention are given e.g. in an aqueous solution or suspension as a dosage unit containing from 0.1 g to 1 g of the compound, calculated as the free acid to be dissolved or suspended immediately before use, or ready for use together with a pharmaceutically acceptable vehicle.

In the form of a dosage unit the compound may be administered once or more times a day at appropriate intervals, always depending, however, on the condition of the patient. As used herein the term "patient" includes animals as well as humans.

Thus, a daily dose will preferably amount to from 0.2 g to 30 g of the compound of the invention calculated as free acid.

The compounds of the invention are appropriately administered in the form of their pharmaceutically acceptable, non-toxic, easily hydrolyzable esters.

The term "non-toxic" for easily hydrolyzable esters shall mean that such esters are therapeutically acceptable for their intended form of administration. In general the easily hydrolyzable esters of the compounds of the invention are used in the oral administration, but their use in the parenteral administration is also within the scope of the invention.

The invention will be further described in the following Examples which are not construed as limiting the invention.

EXAMPLE 1

6-[4'-(3"aminopropyl)-1'-piperidyl-methleneamino]-penicillanic acid monohydrochloride A. 4-(3'-bromopropyl)-piperidine hydrobromide A solution of 4-(3'-hydroxypropyl)-piperidine (10 g) in 47% hydrobromic acid (35 ml) was evaporated to dryness to yield 4-(3'-hydroxypropyl)-piperidine hydrobromide which was treated with phosphorous tribromide (10 ml) for 30 minutes on a steam bath. After cooling, the mixture was extracted with ether (2×100 ml). The ether-insoluble material was extracted with hot absolute ethanol and filtered. The desired compound crystallized from the filtrate when ether was added. Melting point 118°-119° C. The IR-spectrum (KBr) showed strong bands at 1575 and 1440 cm$^{-1}$.

B. 4-(3'-azidopropyl)-piperidine

Sodium azide (1 g) was added to a mixture of 4-(3'-bromopropyl)-piperidine hydrobromide (2 g), water (7 ml) and methanol (7 ml). The pH of the mixture was adjusted to 6.3, and the resulting solution was refluxed for 2 hours. After cooling, methanol was evaporated, 30 percent aqueous sodium hydroxide was added and the mixture was extracted several times with ether. The ether extracts were dried and evaporated to leave the desired compound as an oil. The IR-spectrum (CHCl$_3$) showed strong bands at 2925, 2100 and 1450 cm$^{-1}$.

C. N-formyl-4-(3'-azidopropyl)-piperidine

A solution of 4-(3'-azidopropyl)-piperidine (1.5 g) in methyl formate (5 ml) was refluxed for 1 hour. Evaporation to dryness gave the desired compound as an oil. The IR-spectrum (CHCl$_3$) showed strong bands at 2100, 1660, 1440 and 1270 cm$^{-1}$.

D.

6-[4'-(3"-azidopropyl)-1'-piperidyl-methyleneamino]-penicillanic acid

A solution of N-formyl-4-(3'-azidopropyl)-piperidine (0.96 g) in alcohol-free chloroform was cooled to −20° C. and oxalyl chloride (0.38 ml) was added dropwise. The mixture was kept at −20° C. for 1 hour. The resulting solution is called (A). In the meantime 6-aminopenicillanic acid (0.96 g) was suspended in alcohol-free chloroform (11 ml) and trimethylchlorosilane (1.13 ml) was added. After stirring for 15 minutes, triethylamine (1.25 ml) was added. After stirring for a further 15 minutes, a clear solution was obtained. This solution was cooled to −70° C. and the above prepared solution (A) was added dropwise at −70° to −60° C. Then triethylamine (1.25 ml) was added and stirring continued for 1 hour while the temperature was allowed to raise to −10° C. The solvent was evaporated and the residue was extracted with dry ether (2×25 ml). The ether extracts were filtered in the absence of moisture and the filtrate was shaken with water (20 ml). The aqueous phase was separated and freeze-dried to yield the desired compound as an amorphous powder. The NMR-spectrum (D$_2$O) showed signals at δ=1.58 (s), 1.73 (s), 1.0–2.3 (m), 3.37 (bt), 3.1–4.2 (m), 4.32 (s), 5.45 (d, J=4), 5.63 (d, J=4) and 7.96 (bs) ppm. TMS was used as external reference.

Antibiotic activity: IC$_{50}$ (μg/ml): E.coli [HA2]: 0.04, Salmonella typhimurium [NCTC 5710]: 0.5.

E.

6-[4'-(3"-aminopropyl)-1'-piperidyl-methyleneamino]-penicillanic acid monohydrochloride (EB 686)

A solution of 6-[4'-(3"-azidopropyl)-1'-piperidylmethyleneamino]-penicillanic acid (0.82 g) in water (50 ml) was placed in a 100 ml flask equipped with an efficient stirrer, gas inlet and outlet tubes, a glass-calomel combination electrode, and a burette controlled by an automatic titrator. 10% Pd-C (0.4 g) was added and hydrogen bubbled through the mixture with stirring, a pH-value of 5 being maintained by the addition of 0.1 N hydrochloric acid via the titrator. When the consumption of acid stopped the catalyst was filtered off and the filtrate was freeze-dried to yield the desired compound as an amorphous powder. The NMR-spectrum (D$_2$O) showed signals at δ=1.58 (s), 1.73 (s), 0.9–2.2 (m), 3.06 (bt), 3.1–4.3 (m), 4.33 (s), 5.46 (d, J=4), 5.63 (d, J=4) and 7.98 (bs) ppm. TMS was used as external reference.

EXAMPLE 2

6-[4'-aminomethyl-1'-piperidyl-methyleneamino]-penicillanic acid, monohydrochloride

A. 4-Bromomethyl-piperidine hydrobromide

This compound was prepared as described in Example 1A by substituting 4-hydroxymethyl-piperidine for 4-(3'-hydroxypropyl)-piperidine. It was crystallized from absolute ethanol. M.p.: 134.5°–136.5° C.

B. 4-Azidomethyl-piperidine hydrochloride

Prepared as described in Example 1B by substituting 4-bromomethyl-piperidine hydrobromide for 4-(3'-bromopropyl)-piperidine hydrobromide. It was converted into a hydrochloride which was recrystallized from absolute ethanol-ether. M.p.: 173°–175° C. (d). The IR-spectrum (KBr) showed a strong band at 2100 cm$^{-1}$.

C. N-formyl-4-azidomethyl-piperidine

This compound was prepared as described in Example 1C by substituting 4-azidomethyl-piperidine (freed from its hydrochloride) for 4-(3'-azidopropyl)-piperidine. It was obtained as a colourless oil. The IR-spectrum (CHCl$_3$) showed strong bands at 2100 and 1660 cm$^{-1}$.

D. 6-[4'-azidomethyl-1'-piperidyl-methyleneamino]-penicillanic acid

The compound was prepared as described in Example 1D by substituting N-formyl-4-azidomethyl-piperidine form N-formyl-4-(3'-azidopropyl)-piperidine. It was obtained as a freeze-dried amorphous powder. The NMR-spectrum (D$_2$O), TMS as external standard) showed peaks at $\delta = 1.57$ (s); 1.73 (s); 1.2–2.3 (m); 3.0–4.1 (m); 3.37 (d, J=6); 4.38 (s); 5.47 (d, J=4); 5.63 (d, J=4) and 7.98 (s) ppm.

Antibiotic activity: IC$_{50}$(µg/ml): E.coli [HA2]: 0.05, Salmonella typhimurium [NCTC 5710]: 0.2.

E. 6-[4'-aminomethyl-1'-piperidyl-methyleneamino]-penicillanic acid, monohydrochloride This compound was prepared as described in Example 1E by substituting the compound prepared in Example 2D for that prepared in Example 1D. Colourless amorphous powder. The NMR-spectrum (D$_2$O, TMS as external standard) showed peaks at $\delta = 1.57$ (s); 1.73 (s); 1.2–2.4 (m); 3.03 (d, J=6); 3.2–4.3 (m); 4.33 (s); 5.48 (bd, J=4); 5.65 (d, J=4) and 8.02 (s) ppm.

EXAMPLE 3

Pivaloyloxymethyl 6-[2'-(3''-aminopropyl)-1'-piperidyl-methyleneamino]-penicillanate, dihydrochloride

A. 2-(3'-Bromopropyl)-piperidine hydrobromide

Prepared as described in Example 1A by using 2-(3'-hydroxypropyl)-piperidine instead of 4-(3'-hydroxypropyl)-piperidine. It was crystallized from absolute ethanol-ether. M.p.: 171°–174° C.

B. 2-(3'-Azidopropyl)-piperidine

Prepared as described in Example 1B by substituting 2-(3'-bromopropyl)-piperidine hydrobromide for 4-(3'-bromopropyl)-piperidine hydrobromide. Oil. The IR-spectrum (CHCl$_3$) showed a strong band at 2100 cm$^{-1}$.

C. N-thioformyl-2-(3'-azidopropyl)-piperidine

To a solution of 2-(3'-azidopropyl)-piperidine (1.8 g) in ether (10 ml) was added ethyl thioformate (1.5 ml). The solution was kept at 4° C. overnight and evaporated to leave an oil which was purified by chromatograpy on silica gel. The IR-spectrum (CHCl$_3$) showed strong bands at 2950, 2100, 1485, 1445 and 1250 cm$^{-1}$.

D. Pivaloyloxymethyl 6-[2'-(3''-azidopropyl)-1'-piperidyl-methyleneamino]-penicillanate To an ice-cold solution of N-thioformyl-2-(3'-azidopropyl)-piperidine (0.7 g) in methylene chloride (5 ml) was added triethyloxonium tetrafluoroborate (0.69 g) with stirring. The solution was kept at room temperature for half an hour, cooled in ice and treated with an ice-cold mixture of pivaloyloxymethyl 6-aminopencillanate (1 g, methylene chloride (5 ml) and N,N-diisopropylethylamine (0.62 ml). The resulting solution was concentrated very slowly at 0° C. in vacuo. After 2 hours all the solvent was evaporated. The residue was extracted with ether (3×50 ml). The ether extract was dried and evaporated to yield the desired compound as a colourless oil. The NMR-spectrum (CDCl$_3$, TMS as internal standard) showed peaks at $\delta = 1.22$ (s); 1.50 (s); 1.64 (s); 1.3–2.0 (m); 2.7–4.2 (m); 3.33 (m); 4.37 (s) and 4.42 (s); 5.05 (m); 5.45 (m); 5.76 (d, J=5.5); 5.90 (d, J=5.5); 7.55 and 7.62 (bs) ppm. According to the NMR-spectrum the compound was an approximately 1:1 mixture of the two possible diastereomers.

E. Pivaloyloxymethyl 6-[2'-(3''-aminopropyl)-1'-piperidyl-methyleneamino]-penicillanate, dihydrochloride To a stirred solution of the compound prepared in Example 3D (0.8 g) in ethyl acetate (30 ml), water (30 ml) and hydrochloric acid were added to pH=3. Pd on carbon (10%) (0.4 g) was added and hydrogen was bubbled through the stirred mixture, a pH-value of 3 being maintained by the addition of hydrochloric acid. When the consumption of acid ceased the catalyst was filtered off. The aqueous phase was separated and freeze-dried to yield the desired compound as an amorphous powder. The NMR-spectrum (CD$_3$OD, TMS as internal standard) showed peaks at $\delta = 1.22$ (s); 1.57 (s); 1.75 (s); 1.3–2.2 (m); 3.2–4.1 (m); 3.03 (m); 4.59 (s); 5.5–5.7 (m); 5.93 (d, J=5.5); 5.77 (d, J=5.5) and 8.2 (m) ppm. According to the NMR-spectrum the product was an approximately 1:1 mixture of the two possible diastereomers.

EXAMPLE 4

Pivaloyloxymethyl 6-[4'-(2''-aminoethyl)-1'-piperidylmethyleneamino]-penicillanate, dihydrochloride

A. Pivaloyloxymethyl 6-[4'-(2''-azidoethyl)-1'-piperidyl-methyleneamino]-penicillanate This compound was prepared as described in Example 3D by substituting N-thioformyl-4-(2'-azidoethyl)-piperidine [prepared by following the procedures described in Examples 3A, 3B and 3C and substituting 4-(2'-hydroxyethyl)-piperidine for 2-(3'-hydroxypropyl)-piperidine] for N-thioformyl-2-(3'-azidopropyl)-piperidine. The NMR-spectrum (CDCl$_3$, TMS as internal standard) showed peaks at $\delta = 1.22$ (s), 1.48 (s), 1.63 (s), 0.8–2.1 (m), 3.30 (m), 2.80 (m), 3.70 (m), 4.37 (s), 5.02 (bd), 5.42 (d, J=4), 5.73 (d, J=6), 5.87 (d, J=6), and 7.53 (s) ppm.

B. Pivaloyloxymethyl 6-[4'-(2''-aminoethyl)-1'-piperidyl-methyleneamino]-penicillanate, dihydrochloride This compound was prepared as described in Example 3E by substituting the compound of Example 4A for that of Example 3D. It was obtained as a colourless powder. The NMR-spectrum (CH$_3$OD, TMS as internal standard) showed peaks at $\delta = 1.20$ (s), 1.55 (s), 1.72 (s), 1.1–2.3 (m), 3.02 (m), 3.2–4.2 (m), 4.55 (s), 5.55 (m), 5.77 (d, J=6), 5.90 (d, J=6) and 8.13 (bs) ppm.

EXAMPLE 5

6-(3'-aminomethyl-1'-piperidyl-methyleneamino)-penicillanic acid, monohydrochloride

A. 6-(3'-azidomethyl-1'-piperidyl-methyleneamino)-penicillanic acid

This compound was prepared as described in Example 1D by substituting N-formyl-3-(azidomethyl)-piperidine [prepared by following the procedures described in Examples 1A, 1B, and 1C and substituting 3-(hydroxymethyl)-piperidine for 4-(3'-hydroxypropyl)-piperidine] for N-formyl-4-(3'-azidopropyl)-piperidine. The title compound was obtained as a colourless powder. The NMR-spectrum (D$_2$O, TMS as external standard) showed peaks at $\delta = 1.57$ (s), 1.72 (s), 1.1–2.3 (m), 3.40 (m), 3.0–4.1 (m), 4.30 (s), 5.42 (d, J=4), 5.60 (d, J=4) and 7.97 (bs) ppm.

B. 6-(3'-aminomethyl-1'-piperidyl-methyleneamino)-penicillanic acid, monohydrochloride This compound was prepared as described in Example 1E by substituting the compound of Example 5A for that of Example 1D. Colourless amorphous powder. The NMR-spectrum (D$_2$O, TMS as external standard) showed peaks at $\delta = 1.58$ (s), 1.73 (s), 1.1–2.5 (m), 3.08 (d, J=6), 3.0–4.3 (m), 4.32 (s), 5.47 (d, J=4), 5.59 (d, J=4) and 8.02 (s) ppm.

EXAMPLE 6

Pivaloyloxymethyl 6-[(4'-(2''-aminoethyl)-hexahydro-1'H-azepin-1'-yl)-methyleneamino]-penicillanete, dihydrochloride

A. 4-(2'-hydroxyethyl)-hexahydro-1H-azepine

To a stirred slurry of lithium aluminium hydride (5.70 g) in dry tetrahydrofuran (100 ml) was added $\beta$-carbethoxymethyl-caprolactam (10.3 g) in dry tetrahydrofuran (150 ml) over a period of 30 minutes. The mixture was refluxed for 2.5 hours, cooled and treated very slowly with water. The precipitate was filtered off and the filtrate was evaporated to yield the title compound as a viscous oil, which was used in the next step without purification.

B. Pivaloyloxymethyl 6-[(4'-(2''-azidoethyl)-hexahydro-1'H-azepin-1'-yl)-methyleneamino]-penicillanate This compound was prepared as described in Example 3D by substituting N-thioformyl-4-(2'-azidoethyl)-hexahydro-1H-azepin [prepared by following the procedures described in Examples 3A, 3B, and 3C and substituting 4-(2'-hydroxyethyl)-hexahydro-1H-azepine for 2-(3'-hydroxypropyl)-piperidine] for N-thioformyl-2-(3'-azidopropyl)-piperidine. Colourless oil. The IR-spectrum (CHCl$_3$) showed strong bands at 2100, 1760, and 1625 cm$^{-1}$. The NMR-spectrum (CDCl$_3$, TMS as internal standard) showed peaks at $\delta = 1.20$ (s), 1.50 (s), 1.63 (s), 0.9–2.2 (m), 3.30 (t, J=6.5), 3.0–4.0 (m), 4.38 (s), 5.10 (bd, J=4), 5.48 (d, J=4), 5.75 (d, J=6), 5.92 (d, J=6) and 7.65 (bs) ppm.

C. Pivaloyloxymethyl 6-[(4'-(2''-aminoethyl)-hexahydro-1'H-azepin-1'-yl)-methyleneamino]-penicillanate, dihydrochloride This compound was prepared as described in Example 3E by substituting the compound of Example 6B for that of Example 3D. The title compound was obtained as a colourless powder. The IR-spectrum (CHCl$_3$) showed strong bands at 1770 and 1680 cm$^{-1}$. The MNR-spectrum (CD$_3$OD, TMS as internal standard) showed peaks at $\delta = 1.22$ (s), 1.55 (s), 1.72 (s), 0.9–2.3 (m), 3.0 (m), 3.4–4.1 (m), 4.58 (s), 5.60 (m), 5.76 (d, J=6), 5.95 (d, J=6) and 8.23 (bs) ppm.

EXAMPLE 7

Pivaloyloxymethyl 6-[4'-(3''-N,N-dimethylaminopropyl)-1'-piperidyl-methyleneamino]-penicillanate, dihydrochloride

A. 4-(3'-N,N-dimethylaminopropyl)-piperidine, dihydrochloride

To a solution of 4-(3'-N,N-dimethylaminopropyl)-pyridine (15 g) in methanol (80 ml) and water (10 ml) was added concentrated hydrochloric acid (25 ml) and PtO$_2$ (0.5 g). The mixture was hydrogenated until the theoretical amount of hydrogen had been consumed. After filtration the filtrate was evaporated in vacuo. The residue was crystallized from absolute ethanol-ether. Colourless hygroscopic crystals with m.p. 235°–236° C.

B. N-Thioformyl-4-(3'-N,N-dimethylaminopropyl)-piperidine

A solution of 4-(3'-N,N-dimethylaminopropyl)-piperidine (7.2 g, liberated from its dihydrochloride) in methylene chloride (40 ml) was cooled in ice and treated with ethyl thioformate (6.18 ml). The solution was kept at room temperature for 1 hour and evaporated to leave a yellow oil which was used in the next step without purification.

C. Pivaloyloxymethyl 6-[4'-(3''-N,N-dimethylaminopropyl)-1'-piperidyl-methyleneamino]-penicillanate, dihydrochloride This compound was prepared as described in Example 3D by substituting N-thioformyl-4-(3'-N,N-dimethylaminopropyl)-piperidine for N-thioformyl-2-(3'-azidopropyl)-piperidine. The resulting oil was dissolved in ethyl acetate, water was added and the mixture was stirred while hydrochloric acid was added to pH=3. The aqueous phase was separated and freeze-dried to yield the desired compound as a colourless powder. The NMR-spectrum (CD$_3$OD, TMS as internal standard) showed peaks at $\delta = 1.22$ (s), 1.55 (s), 1.73 (s), 2.92 (s), 0.9–2.3 (m), 2.9–4.5 (m), 4.58 (s), 5.56 (d, J=4), 5.67 (d, J=4), 5.80 (d, J=6), 5.95 (d, J=6) and 8.18 (s) ppm.

EXAMPLE 8

Pivaloyloxymethyl 6-[4'-(2''-piperidinoethyl)-1'-piperidyl-methyleneamino]-penicillanate, dihydrochloride this compound was prepared by following the procedures described in Examples 7B and 7C and substituting 4-(2'-piperidinoethyl)-piperidine for 4-(3'-N,N-dimethylaminopropyl)-piperidine. NMR spectrum: (CD₃OD, TMS) δ=1.22 (s), 1.55 (s), 1.73 (s), 1.2–2.3 (m), 2.7–4.3 (m), 4.55 (s), 5.52 (m), 5.60 (d, J=4), 5.76 (d, J=6), 5.91 (d, J=6), and 8.13 (bs) ppm.

EXAMPLE 9

Pivaloyloxymethyl 6-[4'-(3''-aminopropyl)-1'-piperidyl-methyleneamino]-penicillanate, dihydrochloride

A. Pivaloyloxymethyl 6-[4'-(3''-azidopropyl)-1'-piperidyl-methyleneamino]-penicillanate, hydrochloride a solutin of N-formyl-4-(3'-azidopropyl)-piperidine (0.96 g) in alcohol-free chloroform was cooled to −20° C. and oxalyl chloride (0.38 ml) was added dropwise. After 1 hour at −20° C. the solution was added dropwise at −60° C. to −70° C. to a stirred solution of pivaloyloxymethyl 6-aminopenicillanate (1.47 g) in alcohol-free chloroform. Triethylamine (1.25 ml) was added and within the next hour the temperature was gradually raised to −10° C. The solvent was evaporated and the residue was extracted with ether. The ether extract was evaporated to leave an oil which was dissolved in isopropanol and treated with 1N hydrogen chloride in isopropanol to an apparent pH-value of 1. During the addition of hydrochloric acid the desired compound crystallized. Ether was added and the mixture was cooled in ice and filtered to yield colourless crystals with m.p. 146° C. (dec.). The IR-spectrum (KBr) showed strong bands at 2100, 1782, 1770, 1750, and 1690 cm⁻¹. The NMR-spectrum (CD₃OD, TMS as internal standard) showed peaks at δ=1.20 (s), 1.55 (s), 1.72 (s), 0.9–2.2 (m), 2.9–4.4 (m), 4.55 (s), 5.50 (d, J=4.5), 5.61 (d, J=4.5), 5.77 (d, J=6), 5.90 (d, J=6), and 8.10 (bs) ppm.

B. Pivaloyloxymethyl 6-[4'-(3''-aminopropyl)-1'-piperidyl-methyleneamino]-penicillanate, dihydrochloride To a stirred solution of pivaloyloxymethyl 6-[4'-(3''-azidopropyl)-1'-piperidyl-methyleneamino]-penicillanate, hydrochloride (0.5 g) in water (25 ml) and ethyl acetate (25 ml) was added 5% palladium on barium sulphate (0.5 g) and the mixture was hydrogenated as described in Example 3E. The colourless freeze-dried powder crystallized on stirring with ether. The suspension was cooled and filtered to yield the title compound as colourless crystals. The IR-spectrum (KBr) showed strong bands at 1785–1750 and 1690 cm⁻¹. The NMR-spectrum (CD₃OD, TMS as internal standard) showed peaks at δ=1.22 (s), 1.55 (s), 1.72 (s), 0.9–2.2 (m), 2.95 (m), 2.9–4.4 (m), 4.55 (s), 5.53 (d, J=4), 5.60 (d, J=4), 5.78 (d, J=6), 5.91 (d, J=6) and 8.13 (bs) ppm.

EXAMPLE 10

By following the procedures described in Example 9A and 9B and substituting acetoxymethyl 6-aminopenicillanate, α-acetoxyethyl 6-aminopenicillanate, α-ethoxycarbonyloxyethyl 6-aminopenicillanate and phthalidyl 6-aminopenicillanate respectively for pivaloyloxymethyl 6-aminopenicillanate, the following compounds were prepared:

Acetoxymethyl 6-[4'-(3''-aminopropyl)-1'-piperidyl-methyleneamino]-penicillanate, dihydrochloride.

α-Acetoxyethyl 6-[4'-(3''-aminopropyl)-1'-piperidyl-methyleneamino]-penicillanate, dihydrochloride.

α-Ethoxycarbonyloxyethyl 6-[4'-(3''-aminopropyl)-1'-piperidyl-methyleneamino]-penicillanate, dihydrochloride.

Phthalidyl 6-[4'-(3''-aminopropyl)-1'-piperidyl-methyleneamino]-penicillanate, dihydrochloride.

The IR- and NMR-spectra were in accordance with the structures of the compounds.

EXAMPLE 11

Pivaloyloxymethyl 6-(4'-aminomethyl-1'-piperidyl-methyleneamino)-penicillanate, dihydrochloride

A. Pivaloyloxymethyl 6-(4'-azidomethyl-1'-piperidyl-methyleneamino)-penicillanate, hydrochloride This compound was prepared as described in Example 9A by using N-formyl-4-(azidomethyl)-piperidine instead of N-formyl-4-(3'-azidopropyl)-piperidine. It was obtained as colourless crystals with m.p. 147° C. (dec.). The IR-spectrum (KBr) showed strong bands at 2100, 1783, 1770, 1750, and 1693 cm⁻¹.

B. Pivaloyloxymethyl 6-(4'-aminomethyl-1'-piperidyl-methyleneamino)-penicillanate, dihydrochloride This compound was prepared as described in Example 9B by substituting the compound of Example 11A for that of Example 9A. The colourless freeze-dried powder was crystallized from ethanol-ether. Melting point: 197° C. (dec.). The IR-spectrum (KBr) showed strong bands at 1790, 1750, and 1697 cm⁻¹.

EXAMPLE 12

The following compounds were prepared by following the procedures described in Examples 1A, 1B, 1C, 9A, and 9B and substituting 4-(4'-hydroxybutyl)-piperidine, 4-(5'-hydroxypentyl)-piperidine, 4-(2'-hydroxypropyl)-piperidine, 4-(1'-hydroxyethyl)-piperidine and 4-(2'-hydroxybutyl)-piperidine respectively for 4-(3'-hydroxypropyl)-piperidine. The compounds had the NMR-spectra:

A. Pivaloyloxymethyl 6-[4'-(4''-aminobutyl)-1'-piperidyl-methyleneamino]-penicillanate, dihydrochloride.

δ=1.22 (s), 1.55 (s), 1.73 (s), 1.1–2.2 (m), 2.8–4.5 (m), 4.57 (s), 5.53 (d, J=4), 5.63 (d, J=4), 5.78 (d, J=6), 5.92 (d, J=6) and 8.13 (bs) ppm.

B. Pivaloyloxymethyl 6-[4'-(5''-aminopentyl)-1'-piperidyl-methyleneamino]-penicillanate, dihydrochloride.

δ=1.22 (s), 1.55 (s), 1.73 (s), 1.1–2.2 (m), 2.88 (m), 3.2–4.4 (m), 4.56 (s), 5.60 (m), 5.78 (d, J=6), 5.92 (d, J=6), and 8.13 (bs) ppm.

C. Pivaloyloxymethyl 6-[4'-(2''-aminopropyl)-1'-piperidyl-methyleneamino]-penicillanate, dihydrochloride.

δ = 1.23 (s), 1.53 (s), 1.72 (s), 1.36 (d, J = 7), 0.9–2.3 (m), 3.0–4.5 (m), 4.73 (s), 5.53 (d, J = 4), 5.70 (d, J = 4), 5.86 (d, J = 5.5), 6.00 (d, J = 5.5) and 8.00 (bs) ppm.

D. Pivaloyloxymethyl 6-[4'-(1''-aminoethyl)-1'-piperidyl-methyleneamino]-penicillanate, dihydrochloride.

δ = 1.23 (s), 0.8–2.3 (m), 1.55 (s), 1.75 (s), 3.0–4.3 (m), 4.73 (s), 5.53 (m), 5.70 (d, J = 4), 5.85 (d, J = 6), 5.98 (d, J = 6) and 8.00 (bs) ppm.

E. Pivaloyloxymethyl 6-[4'-(2''-aminobutyl)-1'-piperidyl-methyleneamino]-penicillanate, dihydrochloride.

δ = 1.23 (s), 1.55 (s), 1.73 (s), 1.28 (bt), 0.8–2.3 (m), 2.9–4.2 (m), 4.73 (s), 5.4–5.7 (m), 5.82 (d, J = 6), 5.98 (d, J = 6), and 8.00 (bs) ppm.

Preparation of starting materials.

Preparation of 4-(2'-hydroxypropyl)-piperidine

To a stirred solution of 4-(2'-oxopropyl)-pyridine (13.7 g) in methanol (135 ml), sodium borohydride (3.0 g) was added in portions. After stirring for 2 hours, the mixture was taken to dryness in vacuo. The residue was distributed between ethyl acetate and a minimum of water sufficient to dissolve inorganic salts. The organic phase was dried and evaporated to yield 4-(2'-hydroxypropyl)-pyridine as a colourless oil. The oil was dissolved in acetic acid (100 ml) and hydrogenated in the presence of Adam's catalyst (1 g) until 3 equivalents of hydrogen were consumed. The catalyst was removed by filtration and the filtrate was concentrated in vacuo to yield crude 4-(2'-hydroxypropyl)-piperidine which was used directly in the next step. In analogous manner 4-(2'-hydroxybutyl)-piperidine was prepared from 4-(2'-oxobutyl)-pyridine.

EXAMPLE 13

6-[4'-(3''-aminopropyl)-1'-piperidyl-methyleneamino]-penicillanic acid, monohydrochloride

A. Benzyl 6-[4'-(3''-azidopropyl)-1'-piperidyl-methyleneamino]-penicillanate, hydrochloride This compound was prepared as described in Example 9A by substituting benzyl 6-aminopenicillanate for pivaloyloxymethyl 6-aminopenicillanate. Colourless crystals with m.p.: 120° c. (dec.). The NMr-spectrum (CD₃OD, TMS as internal standard) showed peaks at δ = 1.42 (s), 1.68 (s), 0.9–2.3 (m), 3.0–4.5 (m), 3.33 (m), 4.55 (s), 5.33 (s), 5.52 (d, J = 4), 5.60 (d, J = 4), 7.42 (s) and 8.13 (bs) ppm.

B. 6-[4'-(3''-aminopropyl)-1'-piperidyl-methyleneamino]-penicillanic acid, monohydrochloride To a solution of benzyl 6-[4'-(3''-azidopropyl)-1'-piperidyl-methyleneamino]-penicillanate, hydrochloride (1.3 g) in a mixture of water (50 ml) and ethyl acetate (25 ml) was added 5% palladium on barium sulphate (1.0 g) and the mixture was shaken vigorously with hydrogen for 30 minutes. The catalyst was removed by filtration and the aqueous phase was freeze-dried to yield an amorphous powder identical with that described in Example 1E.

EXAMPLE 14

Pivaloyloxymethyl 6-[4'-(3''-azidopropyl)-1'-piperidyl-methyleneamino]-penicillanate, hydrochloride to a solution of 6-[4'-(3''-azidopropyl)-1'-piperidyl-methyleneamino]-penicillanic acid (4.0 g) and triethylamine (2.1 ml) in dimethylformamide (40 ml) chloromethyl pivalate (3.0 g) was added. After standing overnight at room temperature, the mixture was diluted with ethyl acetate (160 ml) and washed several times with water, dried and evaporated to leave an oil which was dissolved in isopropanol and treated with hydrogen chloride in isopropanol as described in Example 9A. The resulting crystals were identical with those prepared in Example 9A.

EXAMPLE 15

Pivaloyloxymethyl 6-[4'-(3''-azidopropyl)-1'-piperidyl-methyleneamino]-penicillanate, hydrochloride To a solution of pivaloyloxymethyl 6-aminopenicillanate (3.3 g) and triethylamine (2.8 ml) in alcohol-free chloroform (35 ml) 1,1-dichlorodimethyl ether (1.1 g) was added at 0° C. After 20 hours at room temperature 4-(3'-azidopropyl)-piperidine (1.7 g) was added, and the solution as kept at 0° C. overnight. The solution was evaporated, and the residue was redissolved in ethyl acetate and water. The organic phase was separated, washed with water, dried and evaporated to leave an oil which was dissolved in isopropanol and treated with hydrogen chloride in isopropanol. The resulting crystals were identical with those prepared in Example 9A.

EXAMPLE 16

6-[4'-(3''-aminopropyl)-1'-piperidyl-methyleneamino]-penicillanoyloxymethyl D-α-aminobenzyl-penicillinate, trihydrochloride

A. Chloromethyl 6-[4'-(3''-azidopropyl)-1'-piperidyl-methyleneamino]-penicillanate To a solution of 6-[4'-(3''-azidopropyl)-1'-piperidyl-methyleneamino]-penicillanic acid (9.1 g) in dimethylformamide (40 ml) triethylamine (4.5 ml) and chloroiodomethane (15 ml) were added. After 3 hours at room temperature the solution was diluted with ethyl acetate (150 ml) and washed several times with water. The organic phase and water was stirred while hydrochloric acid was added to pH = 2.5. The aqueous phase was separated, made alkaline by the additiion of aqueous sodium bicarbonate and extracted with ethyl acetate. The organic phase was dried and evaporated to yield the desired compound as an oil. The IR-spectrum showed strong bands at 2100, 1760 and 1620 cm⁻¹.

B. 6-[4'-(3''-aminopropyl)-1'-piperidyl-methyleneamino]-penicillanoyloxymethyl D-α-aminobenzylpenicillinate, trihydrochloride To a solution of chloromethyl 6-[4'-(3''-azidopropyl)-1'-piperidyl-methyleneamino]-penicillanate (4.4 g) in dimethylformamide (50 ml) potassium D-α-azidobenzylpenicillinate (4.5 g) was added. After stirring at room temperature for 24 hours, the mixture was diluted with ethyl acetate and washed repeatedly with water. The organic phase was stirred with water while hydrochloric acid was added to pH=3. 10% Pd on carbon (3 g) was added and hydrogen was bubbled through the stirred mixture, a pH-value of 3 being maintained by the addition of hydrochloric acid. When the comsumption of acid ceased the catalyst was filtered off. The aqueous phase was separated and freeze-dried to yield the desired compound as an amorphous powder. The IR-spectrum showed strong bands at 1775 and 1685 cm$^{-1}$.

EXAMPLE 17

6-[4'-(3''-aminopropyl)-1'-piperidyl-methyleneamino]-penicillanoyloxymethyl 7-(D-α-aminophenylacetamido)-cephalosporanate, trihydrochloride This compound was prepared by following the procedure described in Example 16B and substituting potassium 7-(D-α-azidophenylacetamido)-cephalosporanate for potassium D-α-azidobenzylpenicillinate. The IR-spectrum showed strong bands at 1775, 1740, and 1685 cm$^{-1}$.

EXAMPLE 18

Pivaloyloxymethyl 6-[4'-(3''-acetamidopropyl)-1'-piperidyl-methyleneamino]-penicillanate, hydrochloride A stirred solution of pivaloyloxymethyl 6-[4'-(3''-aminopropyl)-1'-piperidyl-methyleneamino]-penicillanate, dihydrochloride (0.56 g) in alcohol-free chloroform was cooled to −70° C. and a solution of acetyl chloride (0.072 ml) in alcohol-free chloroform was added dropwise at this temperature. Then triethylamine (0.42 ml) was added dropwise and the stirring was continued for 1 hour while the temperature was raised to −10° C. The solvent was evaporated and the residue was extracted with ether. The ether extract and water was stirred while hydrochloric acid was added to pH=3. The aqueous phase was separated and freeze-dried to yield the desired compound as an amorphous powder. The NMR-spectrum (CD$_3$OD, TMS as internal standard) showed peaks at δ=1.21(s), 1.55(s), 1.72(s), 0.9–2.3(m), 3.15(m), 3.1–4.4(m), 1.92(s), 4.55(s), 5.50 (d, J=4), 5.60 (d, J=4), 5.76 (d, J=6), 5.92 (d, J=6) and 8.10 (bs) ppm.

EXAMPLE 19

Pivaloyloxymethyl 6-[4'-(3''-(N,N-dimethylamino-methyleneamino)-propyl)-1'-piperidyl-methyleneamino]-penicillanate, dihydrochloride.

To a solution of pivaloyloxymethyl 6-[4'-(3''-azidopropyl)-1'-piperidyl-methyleneamino]-penicillanate (0.5 g) (liberated from its hydrochloride) in ethyl acetate (10 ml) was added dimethylformamide dimethylacetal (0.3 ml) and 10% Pd on carbon (0.25 g). The mixture was hydrogenated at atmospheric pressure for 1 hour, filtered and the filtrate was washed with water. The organic phase was stirred with water while hydrochloric acid was added to pH=3. The aqueous phase was freeze-dried to yield the desired compound as a colourless powder. The NMR-spectrum (CD$_3$OD), TMS as internal standard showed peaks at δ=1.22(s), 1.55(s), 1.73(s), 0.9–2.2(m), 3.09(s), 3.28(s), 2.9–4.4(m), 4.58(s), 5.58(m), 5.80 (d, J=6), 5.93 (d, J=6) and 8.13(m) ppm.

EXAMPLE 20

Pivaloyloxymethyl 6-[4'-(3''-(hexahydro-1'' H-azepin-1'''-yl-methyleneamino)-propyl)-1'-piperidyl-methyleneamino]-penicillanate, dihydrochloride.

This compound was prepared as described in Example 19 by substituting N-formyl-hexamethylenimine-dimethylacetal for dimethylformamide dimethylacetal. The IR-spectrum showed strong bands at 1785–1750 and 1685 cm$^{-1}$.

EXAMPLE 21

Pivaloyloxymethyl 6-[4'-(3''-(3'''-benzoyl-1'''-ureido)-propyl)-1'-piperidyl-methyleneamino]-penicillanate.

To an ice-cold solution of pivaloyloxymethyl 6-[4'-(3''-aminopropyl)-1'-piperidyl-methyleneamino]-penicillanate, dihydrochloride (1.11 g) in dry methylene chloride (25 ml) N,N-diisopropylethylamine (0.8 ml) and benzoyl isocyanate (0.3 ml) were added. After stirring for 2.5 hours at room temperature the mixture was filtered. The filtrate was washed with water, dried and evaporated to leave the title compound as an oil. The NMR-sectrum (CDCl$_3$, TMS as internal standard) showed peaks at δ=1.21(s), 1.50(s), 1.67(s), 0.9–2.3(m), 2.3–4.1(m), 3.38 (q, J=6), 4.42(s), 5.08 (bd, J=4), 5.50 (d, J=4), 5.77 (d, J=6), 5.95 (d, J=6), 7.3–8.1(m), 8.80 (bt) and 9.27(s) ppm.

EXAMPLE 22

Pivaloyloxymethyl 6-[(4'-(2''-(3'''-methyl-1'''-ureido)-ethyl)-hexahydro-1'H-azepin-1'-yl)-methyleneamino]-penicillanate.

A solution of pivaloyloxymethyl 6-[(4'-(2''-aminoethyl)-hexahydro-1'H-azepin-1'-yl)-methyleneamino]-penicillanate, dihydrochloride (0.55 g) and N,N-diisopropylethylamino (0.6 ml) in dry methylene chloride (25 ml) was cooled to −35° C. Methyl isocyanate was added in one portion and the mixture was stirred for 2.5 hours while the temperature was allowed to raise to room temperature. The mixture was washed with water, dried and evaporated to yield the title compound as a yellow oil. The NMR-spectrum (CDCl$_3$, TMS as internal standard) showed peaks at δ=1.23(s), 1.52(s), 1.67(s), 0.8–2.1(m), 2.75 (d, J=4), 2.9–3.6(m), 4.39(s), 5.06 (d, J=4), 4.93(m), 5.48 (d, J=4), 5.77 (d, J=6), 5.93 (d, J=6) and 7.60 (bs) ppm.

EXAMPLE 23

Pivaloyloxymethyl 6-[(4'-(2''-(3'''-phenyl-1'''-ureido)-ethyl)-hexahydro-1'H-azepin-1'-yl)-methyleneamino]-penicillanate.

By following the procedure of Example 22 but substituting phenyl isocyanate for methyl isocyanate, the title compound was obtained as a pale yellow oil. The NMR-spectrum (CDCl$_3$, TMS as internal standard) showed peaks at δ=1.22(s), 1.50(s), 1.65(s), 0.8–2.2(m), 3.0—3.8(m), 4.39(s), 5.03(m), 5.46 (d, J=4.5), 5.73 (d, J=6), 5.92 (d, J=6), 6.8–7.8(m) and 7.55 (bs) ppm.

EXAMPLE 24

Pivaloyloxymethyl 6-[(4'-(2''-ethoxycarbonylamino-ethyl)-hexahydro-1'H-azepin-1'-yl)-methyleneamino]-penicillanate.

By following the procedure of Example 22 but substituting ethyl chloroformate for methyl isocyanate, the title compound was obtained as a yellow oil. The NMR-spectrum (CDCl$_3$, TMS as internal standard) showed signals: $\delta = 1.23$(s), 1.50(s), 1.66(s), 1.66(s), 0.9–2.3(m), 1.36 (t, J=7), 3.0–3.7(m), 4.12 (q, J=7), 4.39(s), 5.09 (d, J=4), 5.48 (d, J=4), 5.75 (d, J=6), 5.90 (d, J=6) and 7.61(s) ppm.

EXAMPLE 25

Pivaloyloxymethyl 6-[(4'-(2''-phenoxycarbonylamino-ethyl)-hexahydro-1'H-azepin-1'-yl)-methyleneamino]-penicillanate.

This compound was obtained as a yellow foam by following the procedure described in Example 22 but substituting phenyl chloroformate for methyl isocyanate. The NMR-spectrum (CDCl$_3$, TMS as internal standard) showed signals at $\delta = 1.23$(s), 1.52(s), 1.67(s), 0.8–2.1(m), 3.1–3.9(m), 4.42(s), 5.10 (d, J=4), 5.50 (d, J=4), 5.77 (d, J=6), 5.93 (d, J=6), 7.0–7.7(m) and 7.65(s) ppm.

EXAMPLE 26

Bis(6-[4'-(3''-aminopropyl)-1'-piperidyl-methyleneamino]-penicillanoyloxy)-methane, tetrahydrochloride

A.
Bis(6-[4'-(3''-azidopropyl)-1'-piperidyl-methyleneamino]-penicillanoyloxy)-methane A solution of N-formyl-4-(3'-azidopropyl)-piperidine (0.96 g) in alcohol-free chloroform was cooled to $-20°$ C. and oxalyl chloride (0.38 ml) was added dropwise. After one hour at $-20°$ C. the solution was added dropwise at $-60°$ to $-70°$ C. to a stirred solution of bis(6-aminopenicillanoyloxy)-methane (1 g) in alcohol-free chloroform. Triethylamine (1.25 ml) was added and within the next hour the temperature was gradually raised to $-10°$ C. The solvent was evaporated and the residue was extracted with ethyl acetate. The extract was washed with water, dried and evaporated to yield the title compound as a yellow oil. The IR-spectrum (CHCl$_3$) showed strong bands at 2100, 1765 and 1630 cm$^{-1}$. The NMR-spectrum (CDCl$_3$, TMS as internal standard) showed peaks at $\delta = 1.51$(s), 1.68(s), 1.0–2.2(m), 3.26(t), 2.6–3.2(m), 3.7–4.2(m), 4.38 (s), 5.03(d, J=4), 5.43 (d, J=4), 5.87(s), and 7.53(s) ppm.

B.
Bis(6-[4'-(3''-aminopropyl)-1'-piperidyl-methyleneamino]-penicillanoyloxy)-methane, tetrahydrochloride To a stirred solution of bis(6-[4'-(3''-azidopropyl)-1'-piperidyl-methyleneamino]-penicillanoyloxy)-methane (0.9 g) in ethyl acetate (35 ml) water (35 ml) and hydrochloric acid were added to pH=3.5% Pd on barium sulphate (0.75 g) was added and the mixture was hydrogenated as described in Example 3 E. The desired compound was obtained as a light yellow freeze-dried powder. The IR-spectrum (KBr) showed strong bands at 1775 and 1690 cm$^{-1}$.

The NMR-spectrum (CD$_3$OD, TMS as internal standard) showed peaks at $\delta = 1.58$(s), 1.75(s), 1.0–2.3(m), 3.0(m), 3.2–4.4(m), 4.63(s), 5.63(m), 6.00(s) and 8.21(s) ppm.

EXAMPLE 27

Bis(6-[4'-aminomethyl-1'-piperidyl-methyleneamino]-penicillanoyloxy)-methane, tetrahydrochloride Following the procedure of Example 26, steps A and B, but substituting N-formyl-4-azidomethylpiperidine for N-formyl-4-(3'-azidopropyl)-piperidine the desired compound was obtained.

The NMR spectrum (CD$_3$OD, TMS as internal standard) showed peaks at $\delta = 1.56$(s), 1.75(s), 3.00(m), 1.2–2.5 (m), 2.9–4.7(m), 4.63(s), 5.63(m), 6.00(m), and 8.26(s) ppm.

EXAMPLE 28

Pivaloyloxymethyl 6-[(4'-(1'',3''-diaminopropyl-2'')-hexahydro-1'H-azepin-1'-yl)-methyleneamino]-penicillanate, trihydrochloride

A. 4(1',3'-dihydroxypropyl-2')-hexahydro-1H-azepine

To suspension of lithium aluminum hydride (5.70 g) in tetrahydrofuran (100 ml), $\beta$-(dicarbethoxymethyl)-caprolactam (13.0 g) in tetrahydrofuran (100 ml) was added dropwise over 30 minutes under a nitrogen atmosphere.

The reaction mixture was refluxed for 2½ hour and cooled to room temperature. Excess of lithium aluminum hydride was destroyed by very slow addition of water. The precipitate formed was filtered off and the filtrate was evaporated in vacuo to give a residue sufficiently pure for the next step.

B. 4-(1',3'-dibromopropyl-2')-hexahydro-1H-azepine 4-(1',3'-dihydroxypropyl-2')-hexahydro-1H-azepine (8.84 g) was dissolved in 48% hydrobromic acid (20 ml) and the solution was evaporated to dryness in vacuo. To the residue phosphorus tribromide (2 ml) was added, and the mixture was heated on a steam bath for one hour and then cooled to room temperature. Thereafter the residue was extracted with ether (2×200 ml) and crystallized on trituration with propanol-2.

C. 4-(1',3'-diazidopropyl-2')-hexahydro-1H-azepine

To a suspension of 4-(1',3'-dibromopropyl-2')-hexahydro-1H-azepine (3.80 g) in a mixture of water (10 ml) and methanol (10 ml), sodium azide (2.60 g) was added, and the reaction mixture was refluxed on an oil bath for 42 hours. The reaction mixture was then evaporated to half the initial volume and water was added to give a clear solution. 30% NaOH (3 ml) was added and the mixture was extracted with ether (3×25 ml). The ether phase was dried over sodium carbonate and evaporated to dryness.

The NMR-spectrum (CDCl$_3$) showed signals at $\delta = 2.6–3.2$(m), 3.42 (d, J=6), 0.9–2.2(m), 2.60(s) ppm. TMS was used as internal standard.

D.
N-Thioformyl-4-(1',3'-diazidopropyl-2')-hexahydro-1-H-azepine

Following the procedure of Example 3 C but substituting the compound of step C above for 2-(3'-azidopropyl)-piperidine the desired compound was obtained and used in the next step.

The NMR-spectrum (CDCl$_3$) showed signals at δ=1.0–2.3(m), 3.43 (d, J=6), 3.4–4.2(m), and 9.30(s) ppm. TMS was used as internal standard.

E. Pivaloyloxymethyl 6-[(4'-(1'',3''-diazidopropyl-2'')-hexahydro-1'H-azepin-1'-yl)-methyleneamino]-penicillanate Following the procedure of Example 3 D but substituting the compound of step D above for N-thioformyl-2-(3'-azidopropyl)-piperidine the desired compound was obtained.

The NMR-spectrum (CDCl$_3$) showed signals at δ=1.22(s), 1.50(s), 1.67(s), 1.0–2.3(m), 3.1–3.8(m), 3.38 (d, J=6), 4.38(s), 5.10 (d, J=4), 5.48 (d, J=4), 5.73 (d, J=6), 5.90 (d, J=6), and 7.63(s) ppm. TMS was used as internal standard.

F. Pivaloyloxymethyl 6-[(4''-(1'',3''-diaminopropyl-2'')-hexahydro-1'-H-azepin-1'-yl)-methyleneamino]-penicillanate, trihydrochloride Following the procedure of Example 3 E but substituting the compound of step E above for the compound of Example 3 D the desired compound was obtained as an amorphous powder.

The NMR-spectrum (CD$_3$OD) showed signals at δ=1.21(s), 1.55(s), 1.74(s), 1.3–2.4(m), 2.9–3.5(m), 3.2–4.1(m), 4.60(s), 5.62(m), 5.78 (d, J=6), 5.95 (d, J=6), 8.28 (s) ppm. TMS was used as internal standard.

Antibiotic activity: IC$_{50}$(µg/ml): Pseudomonas aeruginosa [BA2]: 20, E.coli [HA2]: 0.05, Salmonella typhimurium [NCTC 5710]: 0.05.

EXAMPLE 29

Pivaloyloxymethyl 6-[(4''-(3''-sulfaminopropyl)-piperidyl-1')-methyleneamino]-pencillanate, trimethylamine salt To a solution of pivaloyloxymethyl 6-[(4'-(3''-azidopropyl)-1'-piperidyl)-methyleneamino]-penicillanate, prepared as described in Example 9 A, (1.0 g) in ethyl acetate (25 ml) triethylamino-sulfur trioxide (0.28 g) and 10% Pd/C (1.0 g) were added. The mixture was hydrogenated at atmospheric pressure for one hour, the catalyst was filtered off, and the filtrate was evaporated in vacuo to yield the desired compound as a yellow foam.

The NMR-spectrum (CDCl$_3$) showed signals at δ=1.23(s), 1.52(s), 1.68(s), 0.8;14 2.1(m), 3.2(s), 2.9–4.3(m), 4.53(s), 5.5–5.8(m), 5.73 (d, J=6), 5.93 (d, J=6), and 7.91(s) ppm. TMS was used as internal standard.

EXAMPLE 30

Pivaloyloxymethyl 6-[(4'-sulfaminomethylpiperidyl-1')-methyleneamino]-penicillanate, trimethylamine salt By following the method described in Example 29, but substituting 6-[(4'-azidomethyl-1'-piperidyl)-methyleneamino]-penicillanate for the corresponding propyl compound the desired compound was obtained.

The NMR spectrum((CD$_3$)$_2$SO) showed signals at δ=1.16(s), 1.44(s), 1.64(s), 1.0–2.0(m), 2.65(m), 3.07(s), 2.8–4.2(m), 4.49(s), 5.52(m), 5.76 (d, J=6), 5.90 (d, J=6), and 8.02(s) ppm. TMS was used as internal standard.

EXAMPLE 31

Pivaloyloxymethyl 6-[(7'-aminoethyl-3'-azabicyclo[3.3.1]nonyl-3')-methyleneamino]-penicillanate, dihydrochloride

A. 7-carbethoxy-3-azabicyclo[3.3.1]nonane-2,4-dione

A mixture of 7-chlorocarbonyl-3-azabicyclo[3.3.1]-nonane-2,4-dione (2 g) and absolute ethanol (25 ml) was left overnight at room temperature and evaporated to leave the desired compound which was used in the next step without purification.

B. Pivaloyloxymethyl 6-[(7'-aminomethyl-3'-azabicyclo[3.3.1]nonyl-3')-methyleneamino]-penicillanate, dihydrochloride By following the procedures described in Examples 6A, 6B, and 6C, and substituting 7-carbethoxy-3-azabicyclo[3.3.1]nonane-2,4-dione for β-carbethoxymethyl-caprolactam, the title compound was obtained as a freeze-dried powder. The IR-spectrum (CHCl$_3$) showed strong bands at 1770 and 1685 cm$^{-1}$.

EXAMPLE 32

Pivaloyloxymethyl 6-[(9'-aminomethyl-3'-azaspiro[5.5]undecyl-3')-methyleneamino]-penicillanate, dihydrochloride

A. 9-Carbomethoxy-3-azaspiro[5.5]undecane-2,4-dione

A mixture of 4-carbomethoxycyclohexane-1,1-diacetic acid anhydride and concentrated aqueous ammonia solution was slowly heated with a free flame until the temperature reached 200° C. where it was kept for 1 hour. After cooling the product was ued in the next step without purification.

B. Pivaloyloxymethyl 6-[(9'-aminomethyl-3'-azaspiro[5.5]undecyl-3')-methyleneamino]-penicillanate, dihydrochloride This compound was prepared by following the procedures described in Examples 6A, 6B, and 6C and substituting (in Example 6A) 9-carbomethoxy-3-azaspiro[5.5]undecane-2,4-dione for β-carbethoxymethyl-carpolactam. The compound was obtained as a freeze-dried powder. The IR-spectrum showed strong bands at 1770 and 1680 cm$^{-1}$.

EXAMPLE 33

Pivaloyloxymethyl 6-[(3'-aminomethyl-8'-azabicyclo[4,3,0]nonyl-8')-methyleneamino[-penicillanate, dihydrochloride

A. 4-Butyloxycarbonyl-1,2-cyclohexanecarboximide

To a solution of 4-butyloxycarbonylphthalimide (15 g) in acetic acid (250 ml), PtO$_2$ (0,5 g) was added, and the mixture was hydrogenated until the theoretical amount of hydrogen had been consumed. After filtration the filtrate was evaporated in vacuo to yield a residue which was used in the next step without purification.

B. Pivaloyloxymethyl 6-[(3'-aminomethyl-8'-azabicyclo-[4,3,0]nonyl-8')-methyleneamino]-penicillanate, dihydrochloride This compound was prepared by following the procedures described in Examples 6A, 6B, and 6C and substituting 4-butyloxycarbonyl-1,2-cyclohexane-carboximide for β-carbethoxymethyl-caprolactam. The product was obtained as a colourless freeze-dried powder. The IR-spectrum showed strong bands at 1770 and 1680 cm$^{-1}$.

EXAMPLE 34

Pivaloyloxymethyl 6-[(2'-aminomethyl-8'-azabicyclo-[4,3,0]nonyl-8')-methyleneamino]-penicillanate, dihydrochloride

A. 3-Methyloxycarbonylphthalimide

To a suspension of 3-carboxyphthalimide (10 g) in ether (50 ml), a solution of diazomethane in ether was added slowly until a faint yellow colouration persisted. Excess of diazomethane was destroyed with acetic acid and the reaction mixture was evaporated to yield the desired compound.

B. Pivaloyloxymethyl 6-[(2'-aminomethyl-8'-azabicyclo[4,3,0]nonyl-8')-methyleneamino]-penicillanate, dihydrochloride This compound was prepared by following the procedure described in Examples 33A and 33B and substituting 3-methyloxycarbonylphthalimide for 4-butyloxycarbonyl-phthalimide. The product was obtained as a colourless freeze-dried powder, the IR-spectrum of which showed strong bands at 1770 and 1680 cm$^{-1}$.

EXAMPLE 35

Pivaloyloxymethyl 6[4'-(aminoacetylamino-methyl)-1'-piperidyl-methyleneamino]-penicillanate, dihydrochloride

A. Pivaloyloxymethyl 6-[4'-(azidoacetylamino-methyl)-1'-piperidyl-methyleneamino]-penicillanate, hydrochloride A stirred suspension of pivaloyloxymethyl 6-(4'-aminomethyl-1'-piperidyl-methyleneamino)-penicillanate, dihydrochloride (1.59 g) in dry methylene chloride (75 ml) was cooled to −70° C. and azidoacetyl chloride (0.39 g) was added. Then triethylamine (1.4 ml) was added and the stirring was continued for 2 hours while the temperature was raised to 0° C. The solvent was evaporated and the residue was shaken with ethyl acetate and water. The organic phase was washed with water and then stirred with fresh water while hydrochloric acid was added to pH=3. The aqueous phase was separated and freeze-dried to yield the desired compound as a colourless powder. The IR-spectrum (KBr) showed strong bands at 2100, 1790–1750 and 1685 cm$^{-1}$. The NMR-spectrum (CDCl$_3$, TMS as internal standard) showed peaks at δ=1.23(s), 1.55(s), 1.73(s), 1.1–2.3(m), 3.26(m), 4.00(s), 3.1–4.3(m), 4.56(s), 5.63(s), 5.80(d, J=6), 5.96 (d, J=6), and 8.00(s) ppm.

B. Pivaloyloxymethyl 6-[4'-(aminoacetylamino-methyl)-1'-piperidyl-methyleneamino]-penicillanate, dihydrochloride To a solution of the compound of Example 35A (0.73 g) in water (50 ml), hydrochloric acid was added to pH=3. Then 10% Pd-C (1 g) was added and hydrogen was bubbled through the stirred mixture, a pH-value of 3 being maintained by the addition of hydrochloric acid. When the consumption of acid ceased the catalyst was filtered off and the filtrate was freeze-dried to yield the title compound as a colourless powder. The IR-spectrum (KBr) showed strong bands at 1790–1755 and 1690 cm$^{-1}$. The NMR-spectrum (D$_2$O, TMS as external standard) showed peaks at δ=1.23(s), 1.53(s), 1.72(s), 3.23(d, J=6), 1.2–2.2(m), 3.81(s), 3.1–4.2(m), 5.43 (d, J=4), 5.70(d, J=4), 5.83(d, J=6), 6.00(d, J=6), and 7.97(s) ppm.

EXAMPLE 36

Pivaloyloxymethyl 6-[4'-(β-aminopropionylamino-methyl)-1'-piperidyl-methyleneamino]-penicillanate, dihydrochloride

A. Pivaloyloxymethyl 6-[4'-(β-azidopropionylamino-methyl)-1'-piperidyl-methyleneamino]-penicillanate, hydrochloride This compound was prepared as described in Example 35A and substituting β-azidopropionyl chloride for azidoacetyl chloride. Colourless powder. The IR-spectrum (KBr) showed strong bands at 2100, 1785–1750 and 1685 cm$^{-1}$. The NMR-spectrum (D$_2$O, TMS as external standard) showed peaks at δ=1.23(s), 1.53(s), 1.72(s), 1.2–2.3(m), 2.60(m), 3.20(m), 3.70(m), 3.0–4.3(m), 4.8(s), 5.53 (d, J=4), 5.70 (d, J=4), 5.86(d, J=6), 6.03(d, J=6) and 8.03(s) ppm.

B. Pivaloyloxymethyl 6-[4'-(β-aminopropionylamino-methyl)-1'-piperidyl-methyleneamino]-penicillanate, dihydrochloride This compound was prepared as described in Example 35B and substituting the compound of Example 36A for that of Example 35A. It was obtained as a freeze-dried powder. The IR-spectrum (KBr) showed strong bands at 1785–1750 and 1685 cm$^{-1}$. The NRM-spectrum (D$_2$O, TMS as external standard) showed peaks at δ=1.22(s), 1.53(s), 1.72(s), 1.1–2.3(m), 2.70(t, J=6), 3.3(m), 2.9–4.3(m), 3.7(s), 5.55(d, J=4), 5.70(d, J=4), 5.85 (d, J=6), 6.00(d, J=6) and 8.02(s) ppm.

EXAMPLE 37

Pivaloyloxymethyl 6-[4'-(3''-azidopropyl)-1'-piperidyl-methyleneamino]-penicillanate, hydrochloride To a solution of pivaloyloxymethyl 6-aminopenicillanate (3.3 g) and N,N-diisopropylethylamine (1.7 ml) in dry chloroform (35 ml) at 0° C. was added 3.2 g of the N-formyl-4-(3'-azidopropyl)-piperidine-dimethyl sulfate complex [prepared according to the method of Bredereck et al. Chem.Ber. 101, 41 (1968)]. After 20 hours at 0°–5° C., the solvent was evaporated and the residue was extracted with ethyl acetate. The ethyl acetate extract was evaporated to leave an oil which was dissolved in isopropanol and treated with 1N hydrogen chloride in isopropanol. The crystalline hydrochloride obtained was identical with that described in Example 9A.

EXAMPLE 38

6-[4'-(3''-azidopropyl)-1'-piperidyl-methyleneamino]-penicillanic acid

A solution of N-formyl-4-(3'-azidopropyl)-piperidine-dimethylacetal (2.4 g) [prepared from N-formyl-4-(3'-azidoproyl)-piperidine-dimethyl sulfate complex according to the method of Bredereck et al. Chem.Ber. 101, 41 (1968)] in dry ether (40 ml) was added slowly to a solution of trimethylsilyl 6-aminopenicillanate (2.8 g) in dry ether (200 ml) at −30° C. with stirring. The temperature was raised to 0° C. within 30 minutes and then the mixture was shaken with water (100 ml). The aqueous phase was separated and freeze-dried to yield a product identical with that described in Example 1D.

Whenever the expression "ether" is used alone it designates diethyl ether.

What we claim is:

1. An antibiotic compound of the general formulae I, II, and III

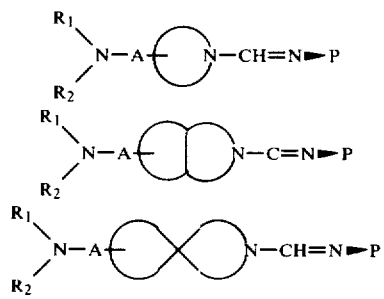

in which -A- stands for a straight or branched, saturated or unsaturated aliphatic hydrocarbon radical, having from 1 to 6 carbon atoms, which radical optionally can be substituted with an amino radical; $R_1$ stands for hydrogen, or a lower alkyl radical having from 1 to 4 carbon atoms; $R_2$ stands for hydrogen, a lower alkyl radical having from 1 to 4 carbon atoms, or a monoacyl radical derived from a mono- or dibasic carboxylic acid, sulphuric acid, a sulphonic acid, a sulphinic acid, phosphoric acid, or a phosphonic acid, and $R_2$ can represent an unsubstituted or a lower alkyl or phenyl substituted radical selected from the group consisting of carbamoyl, guanyl and guanylcarbamoyl radicals; $R_1$ and $R_2$ together with the nitrogen atom can form a monocyclic, saturated ring having from 4 to 8 carbon atoms; furthermore $R_1$ and $R_2$ together can represent a radical of the formula

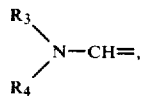

in which $R_3$ and $R_4$ each stands for hydrogen, lower alkyl, phenyl or phenyl-lower alkyl, or in which $R_3$ and $R_4$ together with the nitrogen atom form a monocyclic, saturated ring having from 4 to 7 carbon atoms; the groupings:

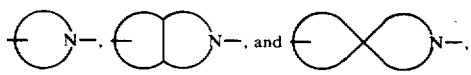

represent saturated, monocyclic, bicyclic or spirocyclic ring systems, respectively, having from 4 to 11 carbon atoms in total; P stands for the penicillanic acid radical of the formula IV:

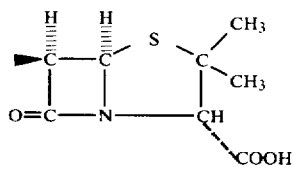

and salts of the compounds of the formulae I, II, and III with pharmaceutically acceptable, non-toxic organic and inorganic acids or bases, and easily hydrolyzable pharmaceutically acceptable, non-toxic esters of the penicillanic acid derivatives of formulae I, II, and III.

2. An antibiotic compound of the general formula I

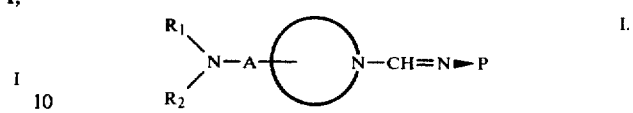

in which -A- stands for a straight or branched, saturated or unsaturated aliphatic hydrocarbon radical, having from 1 to 6 carbon atoms, which radical optionally can be substituted with an amino radical; $R_1$ stands for hydrogen, or a lower alkyl radical having from 1 to 4 carbon atoms; $R_2$ stands for hydrogen, a lower alkyl radical having from 1 to 4 carbon atoms, or a monoacyl radical derived from a mono- or dibasic carboxylic acid, sulphuric acid, a sulphonic acid, a sulphinic acid, phosphoric acid, or a phosphonic acid, and $R_2$ can represent an unsubstituted or a lower alkyl or phenyl substituted radical selected from the group consisting of carbamoyl, guanyl and guanylcarbamoyl radicals; $R_1$ and $R_2$ together with the nitrogen atom can form a monocyclic, saturated ring having from 4 to 8 carbon atoms; furthermore $R_1$ and $R_2$ together can represent a radical of the formula

in which $R_3$ and $R_4$ each stands for hydrogen, lower alkyl, phenyl or phenyl-lower alkyl, or in which $R_3$ and $R_4$ together with the nitrogen ato form a monocyclic, saturated ring having from 4 to 7 carbon atoms; the grouping:

represents a saturated monocyclic ring system having from 4 to 11 carbon atoms; P stands for the penicillanic acid radical of the formula IV:

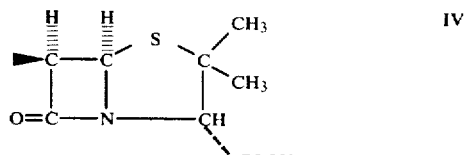

and salts of the compounds of the formula I with pharmaceutically acceptable, non-toxic organic and inorganic acids or bases, and easily hydrolyzable pharmaceutically acceptable, non-toxic esters of the penicillanic acid derivatives of formula I.

3. An antibiotic compound of the general formula II

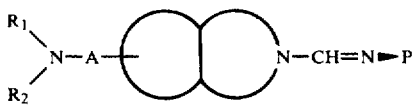

II in which -A- stands for a straight or branched, saturated or unsaturated aliphatic hydrocarbon radical having from 1 to 6 carbon atoms, which radical optionally can be substituted with an amino radical; $R_1$ stands for hydrogen, or a lower alkyl radical having from 1 to 4 carbon atoms; $R_2$ stands for hydrogen, a lower alkyl radical having from 1 to 4 carbon atoms, or a monoacyl radical derived from a mono- or dibasic carboxylic acid, sulphuric acid, a sulphonic acid, a sulphinic acid, phosphoric acid, or a phosphonic acid, and $R_2$ can represent an unsubstituted or a lower alkyl or phenyl substituted radical selected from the group consisting of carbamoyl, guanyl and guanylcarbamoyl radicals; $R_1$ and $R_2$ together with the nitrogen atom can form a monocyclic, saturated ring having from 4 to 8 carbon atoms; furthermore $R_1$ and $R_2$ together can represent a radical of the formula

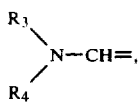

in which $R_3$ and $R_4$ each stands for hydrogen, lower alkyl, phenyl or phenyl-lower alkyl, or in which $R_3$ and $R_4$ together with the nitrogen atom form a monocyclic, saturated ring having from 4 to 7 carbon atoms; the grouping:

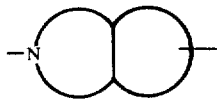

represents a saturated, bicyclic ring system, having from 4 to 11 carbon atoms in total; P stands for the penicillanic acid radical of the formula

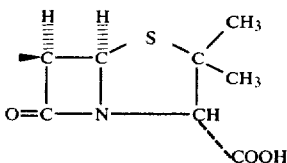

IV and salts of the compounds of the formula II with pharmaceutically acceptable, non-toxic organic and inorganic acids or bases, and easily hydrolyzable pharmaceutically acceptable, non-toxic esters of the penicillanic acid derivatives of formula II.

4. An antibiotic compound of the general formula III

III in which -A- stands for a straight or branched, saturated or unsaturated aliphatic hydrocarbon radical, having from 1 to 6 carbon atoms, which radical optionally can be substituted from an amino radical; $R_1$ stands for hydrogen, or a lower alkyl radical having from 1 to 4 carbon atoms; $R_2$ stands for hydrogen, a lower alkyl radical having from 1 to 4 carbon atoms, or a monoacyl radical derived from a mono- or dibasic carboxylic acid, sulphuric acid, a sulphonic acid, a sulphinic acid, phosphoric acid, or a phosphonic acid, and $R_2$ can represent an unsubstituted or a lower alkyl or phenyl substituted radical selected from the group consisting of carbamoyl, guanyl and guanylcarbamoyl radicals; $R_1$ and $R_2$ together with the nitrogen atom can form a monocyclic, saturated ring having 4 to 8 carbon atoms; furthermore $R_1$ and $R_2$ together can represent a radical of the formula

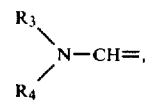

in which $R_3$ and $R_4$ each stands for hydrogen, lower alkyl, phenyl or phenyl-lower alkyl, or in which $R_3$ and $R_4$ together with the nitrogen atom form a monocyclic, saturated ring having from 4 to 7 carbon atoms; the grouping:

represents a saturated spirocyclic ring system having from 4 to 11 carbon atoms in total; P stands for the penicillanic acid radical of the formula

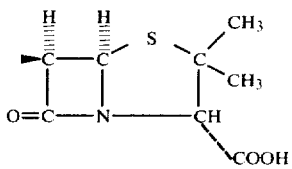

IV and salts of the compounds of the formula III with pharmaceutically acceptable, non-toxic organic and inorganic acids or bases, and easily hydrolyzable pharmaceutically acceptable, non-toxic esters of the penicillanic acid derivatives of formula III.

5. A compound according to claim 2 in which -A- stands for a saturated or unsaturated carbon chain with from 1 to 3 carbon atoms, $R_1$ and $R_2$ stand for hydrogen, and pharmaceutically acceptable, non-toxic salts and easily hydrolyzable esters thereof, and their salts.

6. A compound according to claim 2 in which the grouping

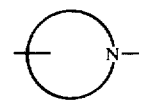

has from 5 to 8 carbon atoms, -A- contains from 1 to 3 carbon atoms and pharmaceutically acceptable, non-toxic salts and easily hydrolyzable esters thereof, and their salts.

7. 6-[4′-aminomethyl-1′-piperidyl-methyleneamino]-penicillanic acid, and pharmaceutically acceptable, non-toxic salts and easily hydrolyzable esters thereof, and their salts.

8. 6-[4′-(3″-aminopropyl)-1′-piperidyl-methyleneamino]-penicillanic acid, and pharmaceutically acceptable, non-toxic salts and easily hydrolyzable esters thereof, and their salts.

9. 6-[4′-(2″-aminoethyl)-hexahydro-1′H-azepin-1′-yl)-methyleneamino]-penicillanic acid, and pharmaceutically acceptable, non-toxic salts and easily hydrolyzable esters thereof, and their salts.

10. 6-[4′-(3″-acetamidopropyl)-1′-piperidyl-methyleneamino]-penicillanic acid, and pharmaceutically acceptable, non-toxic salts and easily hydrolyzable esters thereof, and their salts.

11. 6-[4′-(3″-(N,N-dimethylamino-methyleneamino)-propyl)-1′-piperidyl-methyleneamino]-penicillanic acid, and pharmaceutically acceptable, non-toxic salts and easily hydrolyzable esters thereof, and their salts.

12. Bis-(6-[4′-(3″-aminopropyl)-1′-piperidyl-methyleneamono]-penicillanoyloxy)-methane, and pharmaceutically acceptable, non-toxic salts thereof.

13. 6-[(4′-(1″,3″-diaminopropyl-2″)-hexahydro-1′H-azepin-1′-yl)-methyleneamino]-penicillanic acid, and pharmaceutically acceptable, non-toxic salts and easily hydrolyzable esters thereof, and their salts.

14. A compound according to claim 3 in which -A- stands for a saturated or unsaturated carbon chain with from 1 to 3 carbon atoms, and in which $R_1$ and $R_2$ stand for hydrogen, and pharmaceutically acceptable, non-toxic salts and easily hydrolyzable esters thereof, and their salts.

15. A compound according to claim 3 in which in the grouping

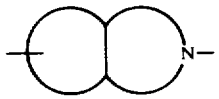

the individual rings have a maximum of 7 carbon atoms, -A- contains from 1 to 3 carbon atoms, and pharmaceutically acceptable, non-toxic salts and easily hydrolyzable esters thereof, and their salts.

16. A compound according to claim 15 in which the numbers of carbon atoms in the heterocyclic part of the ring is 4 and the total number of the carbon atoms in the ring system are 7 or 8.

17. A compound according to claim 4 in which -A- stands for a saturated or unsaturated carbon chain with from 1 to 3 carbon atoms, and in which $R_1$ and $R_2$ stand for hydrogen, and pharmaceutically acceptable, non-toxic salts and easily hydrolyzable esters thereof, and their salts.

18. A compound according to claim 4 in which in the spirocyclic grouping

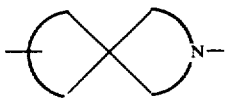

the individual rings have a maximum of 7 carbon atoms, -A- contains from 1 to 3 carbon atoms, and pharmaceutically acceptable, non-toxic salts and easily hydrolyzable esters thereof, and their salts.

19. An antibacterial composition in dosage unit form for enteral or parenteral treatment of patients, which comprises as an active ingredient 0.025 g to 2.5 g of a compound as claimed in claim 2 calculated as the free acid together with a non-toxic pharmaceutically acceptable carrier.

20. An antibacterial composition in dosage unit form as claimed in claim 19 for oral treatment of patients said composition containing from 0.05 g to 1.5 g of the active ingredient, calculated as the free acid.

21. An antibacterial composition in dosage unit form as claimed in claim 20 and containing as the active component the compound 6-[4′-(3″-aminopropyl)-1′-piperidyl-methyleneamino]-penicillanic acid, or a pharmaceutically acceptable, non-toxic salt or easily hydrolyzable ester thereof, or a salt of such ester.

22. An antibacterial composition in dosage unit form as claimed in claim 21 in the form of tablets, pills or capsules.

23. An antibacterial composition in dosage unit form for parenteral treatment of patients, said composition comprising from 0.1 g to 1 g of a compound as claimed in claim 2, calculated as the free acid, as such or in the form of one of its non-toxic salts.

24. An antibacterial composition in dosage unit form as claimed in claim 23 and containing as the active ingredient the compound 6-[4′-(3″-aminopropyl)-1′-piperidyl-methyleneamino]-penicillanic acid, or a pharmaceutically acceptable, non-toxic salt or easily hydrolyzable ester thereof or a salt of such ester.

25. An antibacterial composition for treatment of patients said composition containing as the active ingredient a compound as claimed in claim 2 together with carrier subtances and auxiliary agents, containing from 1% to 95% of the active ingredient, calculated as the free acid.

26. An antibacterial composition for treatment of patients as claimed in claim 25 containing the active ingredient together with an active additive selected from the group consisting of known penicillins, cephalosporins, amidinopenicillanic acid derivatives, aminoglycoside antibiotics, trimethoprim or clavulanic acid, the ratio between the active compounds being between 1:20 and 20:1.

27. An antibacterial composition as claimed in claim 26 in dosage unit form for enteral and parenteral treatment of patients and containing from 0.025 g to 2.5 g in total of the active compounds, as present, in the composition.

28. A method of treating patients suffering from bacterial infections, which comprises administering to said patients a compound as claimed in claim 2 in daily doses from 0.2 to 30 g calculated as the free acid.

29. A compound of claim 2 wherein the penicillanic acid radical of formula IV is esterified, forming a diester of the formula V

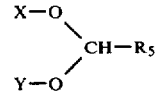

in which X and Y can be the same or different and can stand for an acyl radical of a compound of formula 1, and Y furthermore can be the acyl ester of a conventional β-lactam antibiotic, $R_5$ stands for hydrogen, methyl, ethyl, or phenyl, and salts of such esters with pharmaceutically acceptable, non-toxic acids or bases.

30. A compound according to claim 2, in which R₁ and R₂ are selected from the group consisting of hydrogen and lower alkyl with from 1 to 4 carbon atoms;

A is a straight or branched saturated hydrocarbon radical containing 1-6 carbon atoms which chain may optionally be substituted with an unsubstituted or mono- or di-lower alkylsubstituted amino group, the

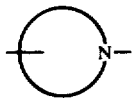

represents a saturated monocyclic ring containing 5-8 carbon atoms, and pharmaceutically acceptable, non-toxic salts and easily hydrolyzable, non-toxic, pharmaceutically acceptably esters thereof and their salts.

31. A compound as in claim 30 wherein R₁ and R₂ are hydrogen or methyl.

32. A compound as in claim 30 wherein R₁ and R₂ are both hydrogen.

33. A compound as in claim 30 wherein A is a straight carbon atom chain containing 1-3 carbon atoms.

34. A compound as in claim 30 wherein A is a branched carbon chain containing 3-6 carbon atoms.

35. A compound as in claim 34 wherein A may optionally be substituted with unsubstituted amino group.

36. A compound as in claim 30 wherein the group

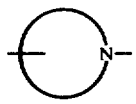

contains 5 or 6 carbon atoms.

37. A compound as in claim 36 wherein the group

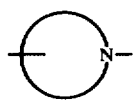

is piperidyl-1.

38. A compound as in claim 36 wherein the group

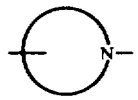

is hexahydro-1H-azepin-1-yl.

39. A compound according to claim 2 in which -A- stands for a saturated or unsaturated hydrocarbon radical with from 1 to 3 carbon atoms, R₁ and R₂ stand for hydrogen, and pharmaceutically acceptable, non-toxic salts and easily hydrolyzable esters thereof, and their salts.

40. A compound according to claim 2 in which the grouping

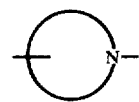

has from 5 to 8 carbon atoms, -A- contains from 1 to 3 carbon atoms, and pharmaceutically acceptable, non-toxic salts and easily hydrolyzable esters thereof, and their salts.

41. 6-[4'-(2''-aminoethyl)-1'-piperidyl-methyleneamino]-penicillanic acid and pharmaceutically acceptable, non-toxic salts and easily hydrolyzable esters thereof, and their salts.

42. 6-[4'-(3''-N,N-Dimethylaminopropyl)-1'-piperidyl-methyleneamino]-penicillanic acid and pharmaceutically acceptable salts and easily hydrolyzable pharmaceutically acceptable esters thereof and their salts.

43. 6-[4'-(2''-Aminobutyl)-1'-piperidylmethyleneamino]-penicillanic acid and pharmaceutically acceptable salts and easily hydrolyzable pharmaceutically acceptable esters thereof and their salts.

44. A compound of claim 1 wherein the penicillanic acid radical of formula IV is esterified, forming a diester of the formula V

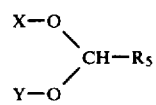

in which X and Y can be the same or different and can stand for an acyl radical of a compound of formulae I, II and III, and Y furthermore can be the acyl ester of a conventional β-lactam antibiotic, R₅ stands for hydrogen, methyl, ethyl, or phenyl, and salts of such esters with pharmaceutically acceptable, non-toxic acids or bases.

45. A compound of claim 3 wherein the penicillanic acid radical of formula IV is esterified, forming a diester for the formula V

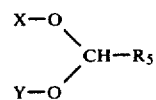

in which X and Y can be the same of different and can stand for an acyl radical of a compound of formula II, and Y furthermore can be the acyl ester of a conventional β-lactam antibiotic, R₅ stands for hydrogen methyl, ethyl, or phenyl, and salts of such esters with pharmaceutically acceptable, non-toxic acids or bases.

46. A compound of claim 4 wherein the penicillanic acid radical of formula IV is esterified, forming a diester of the formula V

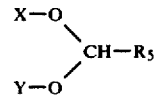

in which X and Y can be the same or different and can stand for an acyl radical of a compound of formula III, and Y furthermore can be the acyl ester of a conventional β-lactam antibiotic, R₅ stands for hydrogen, methyl, ethyl, or phenyl, and salts of such esters with pharmaceutically acceptable, non-toxic acids or bases.

47. An antibacterial composition in dosage unit form for enteral or parenteral treatment of patients, which comprises as an active ingredient 0.025 g to 2.5 g of a compound as claimed in claim 1 calculated as the free acid together with a non-toxic, pharmaceutically acceptable carrier.

48. An antibacterial composition in dosage unit form as claimed in claim 1 for oral treatment of patients containing from 0.05 g to 1.5 g of the active ingredient, calculated as the free acid.

49. An antibacterial composition in dosage unit form for parenteral treatment of patients, said composition comprising from 0.1 g to 1 g of a compound as claimed in claim 1, calculated as the free acid, as such or in the form on one of its non-toxic salts.

50. An antibacterial composition for treatment of patients said composition containing as the active ingredient a compound as claimed in claim 1 together with carrier substances and auxillary agents, containing 1% to 95% of the active ingredient, calculated as the free acid.

51. An antibacterial composition for treatment of patients as claimed in claim 50 containing the active ingredient together with an active additive selected from the group consisting of known penicillins, cephalosporins, amidinopenicillanic acid derivatives, aminoglycoside antibiotics, trimethoprim or clavulanic acid, the ratio between the active compounds being 1:20 and 20:1.

52. An antibacterial composition as claimed in claim 51 in dosage unit form for enteral and parenteral treatment of patients and containing from 0.025 g to 2.5 g in total of the active compounds, as present, in the composition.

53. A method of treating patients suffering from bacterial infection, which comprises administering to said patients a compound as claimed in claim 1 in daily doses from 0.2 to 30 g calculated as the free acid.

54. The pharmaceutical composition as claimed in claim 26 wherein the ratio between the active compounds is between 1:5 and 5:1.

55. The pharmaceutical composition as claimed in claim 51 wherein the ratio between the active compounds is between 1:5 and 5:1.

* * * * *